(12) United States Patent
Argentine

(10) Patent No.: US 8,920,485 B2
(45) Date of Patent: Dec. 30, 2014

(54) STENT-GRAFT DELIVERY SYSTEM HAVING A ROTATABLE SINGLE SHAFT TIP CAPTURE MECHANISM

(75) Inventor: Jeff Argentine, Petaluma, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 278 days.

(21) Appl. No.: 13/447,107

(22) Filed: Apr. 13, 2012

(65) Prior Publication Data

US 2013/0274860 A1    Oct. 17, 2013

(51) Int. Cl.
    *A61F 2/95* (2013.01)
(52) U.S. Cl.
    USPC ........................................ 623/1.12; 623/1.11
(58) Field of Classification Search
    CPC .............. A61F 2/95; A61F 2002/9505; A61F 2002/9665
    USPC ..................... 623/1.11, 1.12, 1.13, 1.23, 2.11; 606/108, 200
    See application file for complete search history.

(56) References Cited

U.S. PATENT DOCUMENTS

| | | |
|---|---|---|
| 5,749,921 A | 5/1998 | Lenker et al. |
| 5,824,041 A | 10/1998 | Lenker et al. |
| 6,350,278 B1 | 2/2002 | Lenker et al. |
| 7,264,632 B2 | 9/2007 | Wright et al. |
| 7,771,463 B2 | 8/2010 | Ton et al. |
| 7,942,924 B1 | 5/2011 | Perez et al. |
| 2004/0148008 A1 | 7/2004 | Goodson, IV et al. |
| 2008/0065011 A1* | 3/2008 | Marchand et al. ........ 604/103.02 |
| 2008/0262590 A1* | 10/2008 | Murray ......................... 623/1.11 |
| 2008/0264102 A1 | 10/2008 | Berra |
| 2009/0276027 A1 | 11/2009 | Glynn |
| 2010/0010617 A1 | 1/2010 | Goodson, IV |
| 2010/0268315 A1 | 10/2010 | Glynn et al. |
| 2011/0251683 A1* | 10/2011 | Tabor ........................... 623/2.11 |
| 2011/0257720 A1 | 10/2011 | Peterson et al. |
| 2012/0221091 A1* | 8/2012 | Hartly et al. ................. 623/1.11 |
| 2013/0131775 A1* | 5/2013 | Hadley et al. ................ 623/1.11 |

FOREIGN PATENT DOCUMENTS

EP    2596770    5/2013

* cited by examiner

*Primary Examiner* — Julian W Woo
*Assistant Examiner* — Lucas Paez

(57) ABSTRACT

A stent-graft delivery system includes an elongate shaft, a tip capture spindle disposed over the shaft, and a distal tip assembly coupled to the distal end of the shaft. At least one component of the delivery system constrains a stent of the stent-graft engaged with the tip capture spindle during delivery and partial-deployment of the stent-graft, and the at least one component is in a threaded relationship with the distal tip assembly. To fully deploy the stent-graft, the elongate shaft, having the distal tip assembly coupled thereto, is rotated to result in longitudinal movement of the at least one component and thereby release the stent from the tip capture spindle. The at least one component that longitudinally moves to fully deploy the stent-graft may be the tip capture spindle and/or a relatively short sleeve that extends over the tip capture spindle to the distal tip assembly.

20 Claims, 13 Drawing Sheets

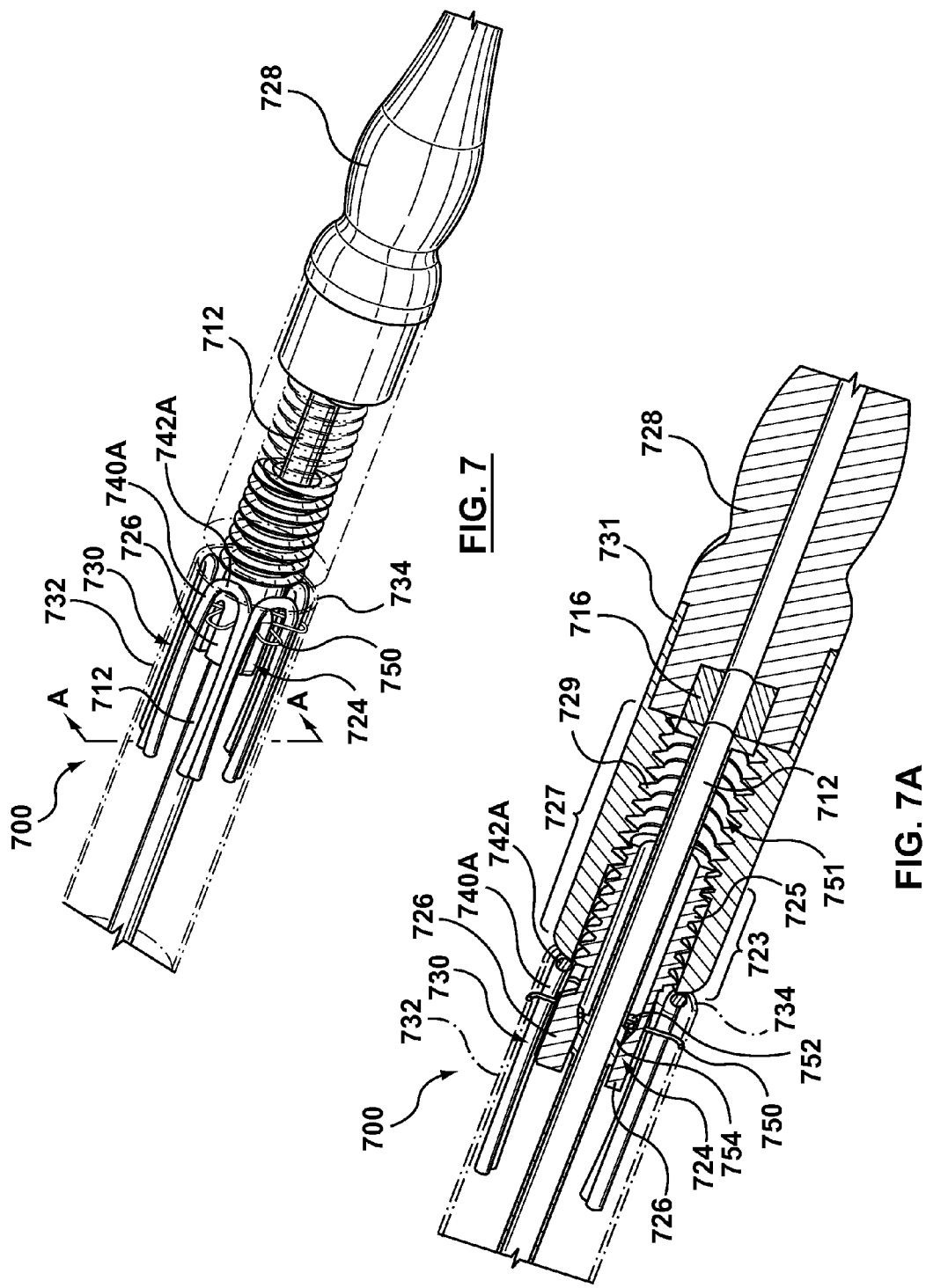

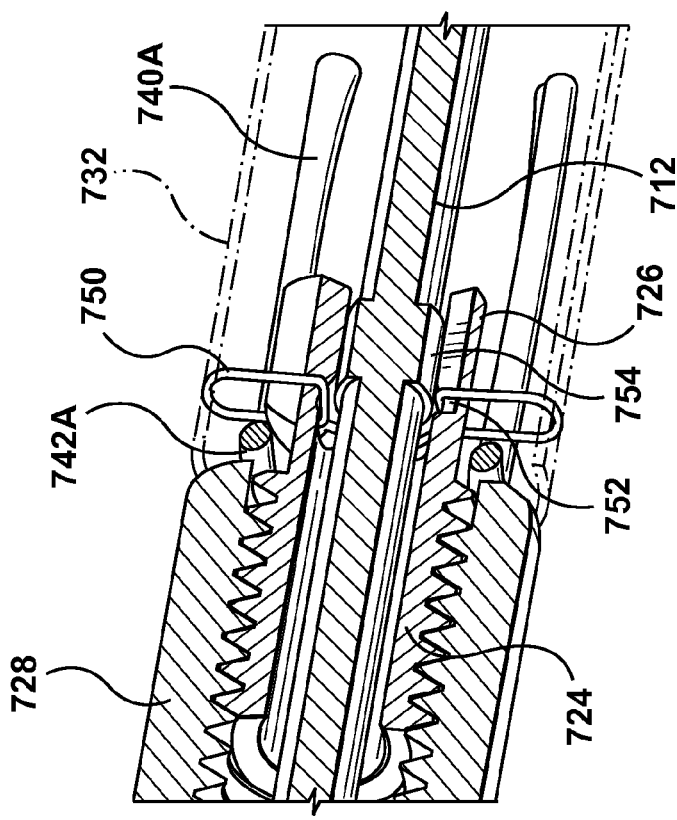
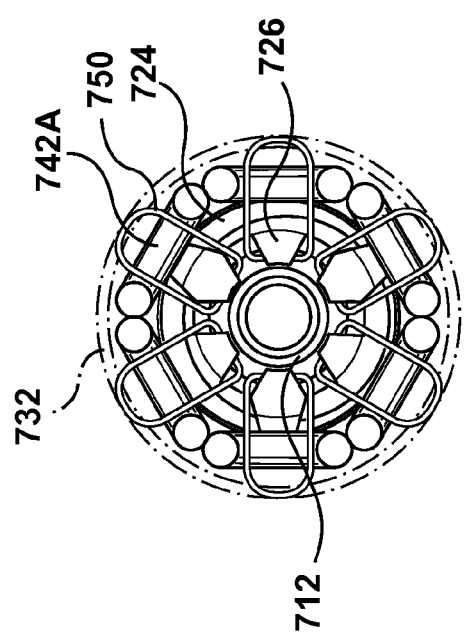

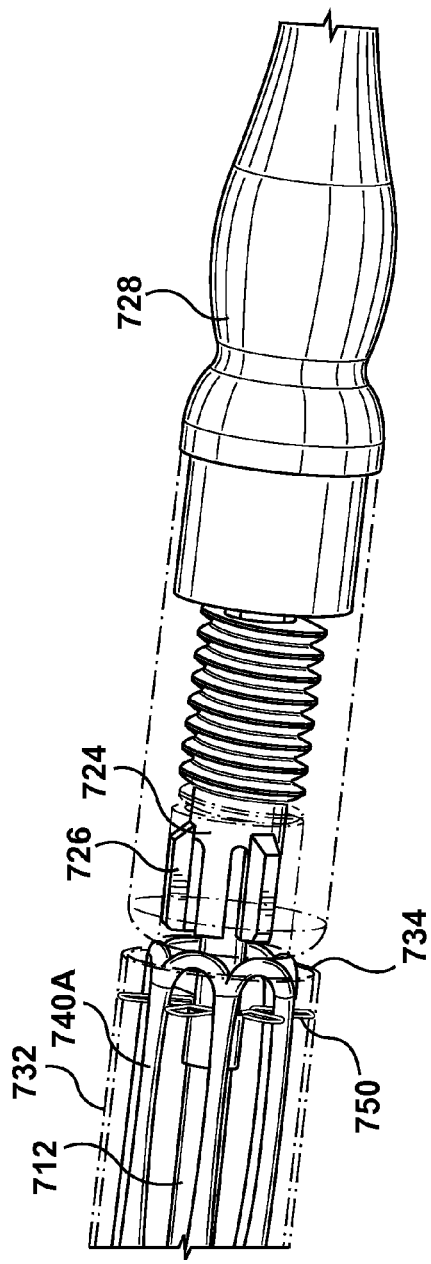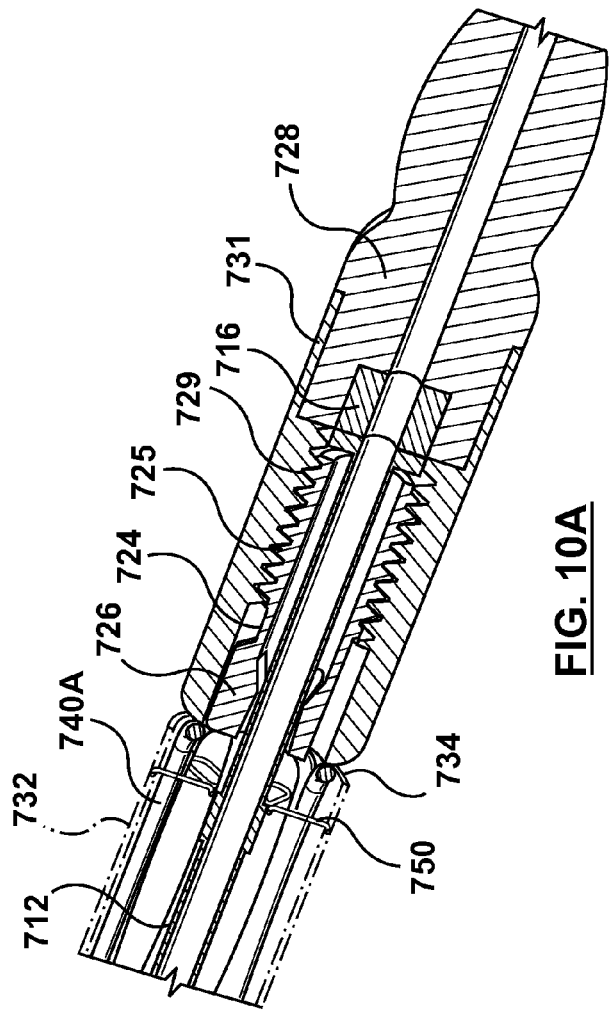

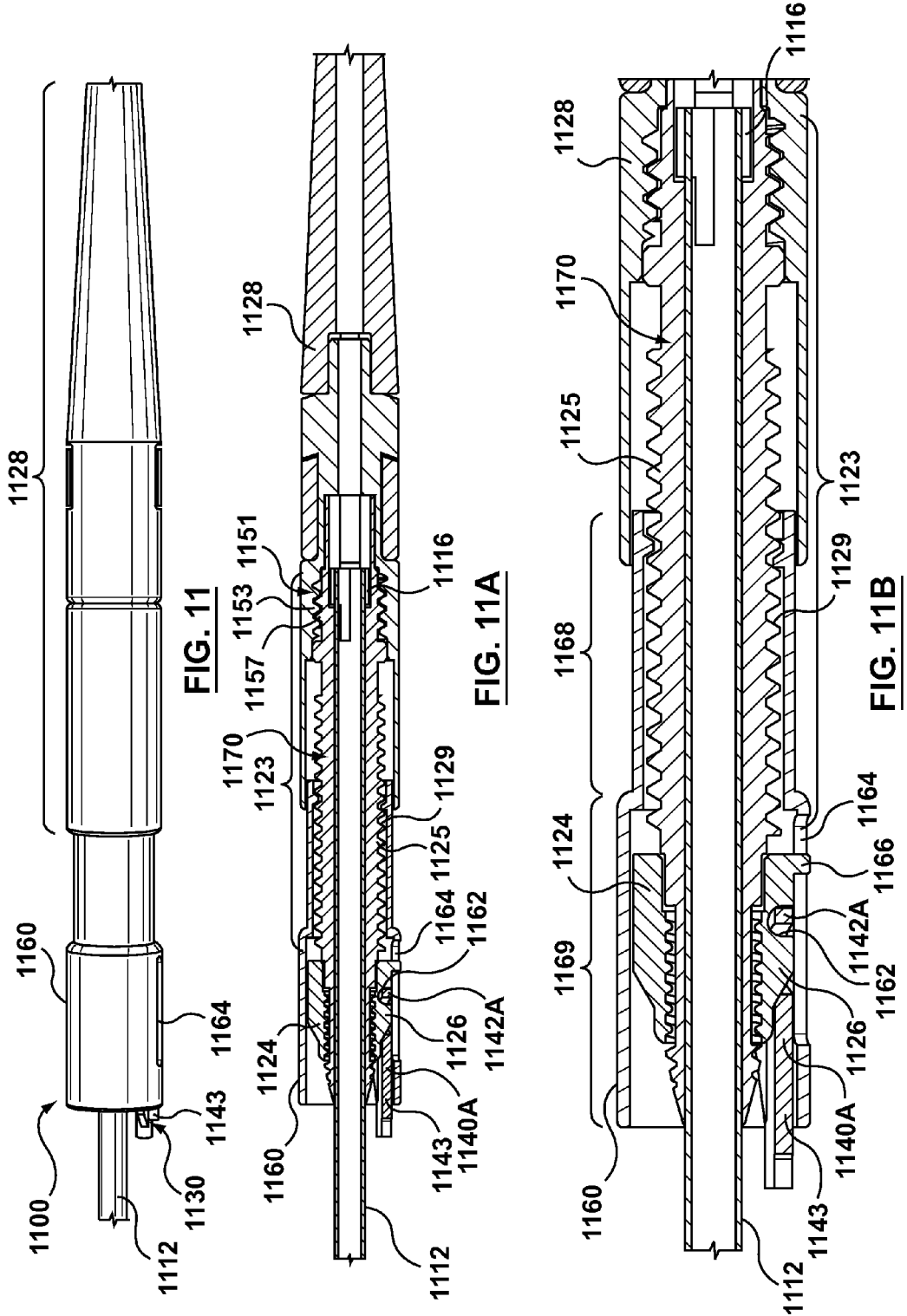

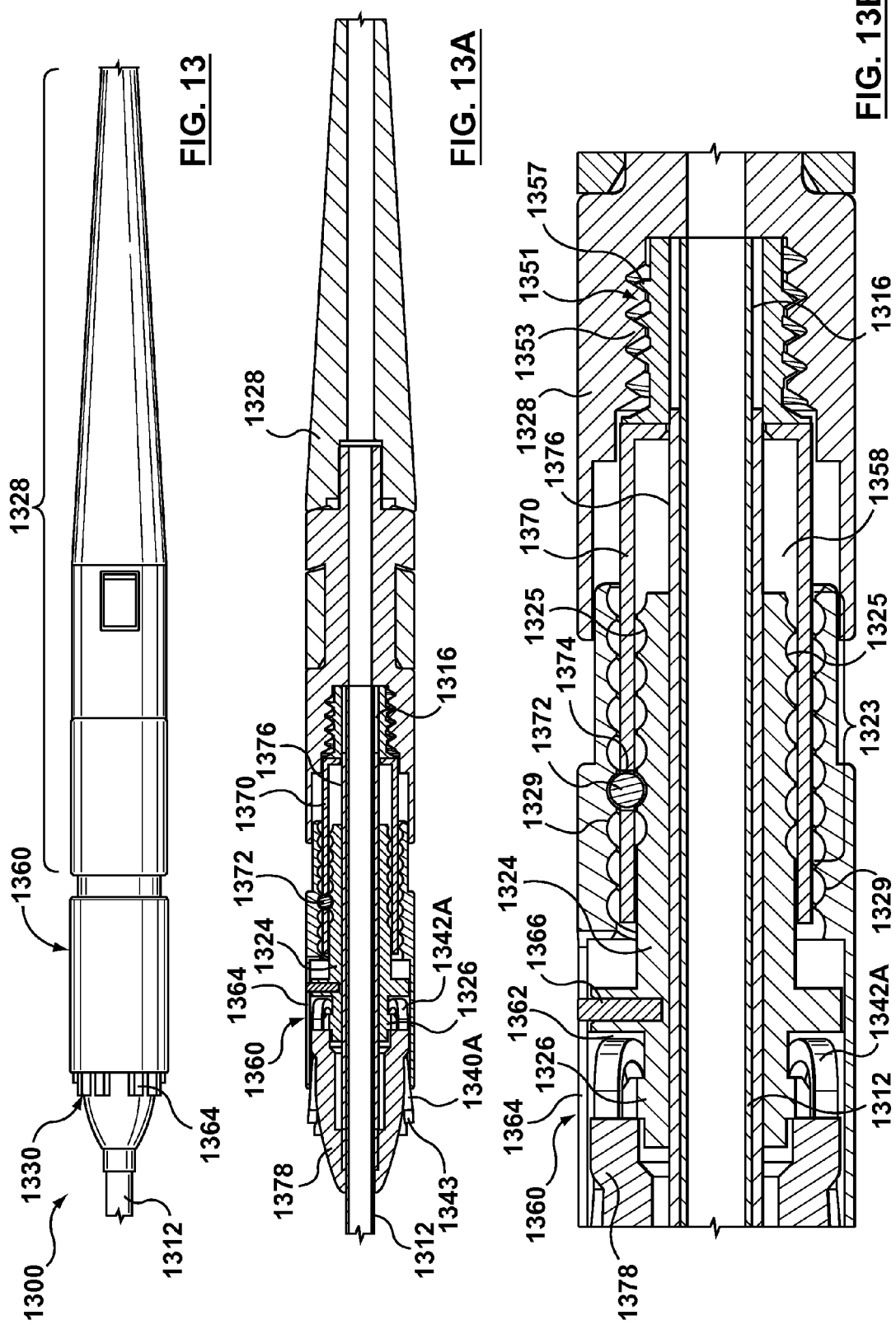

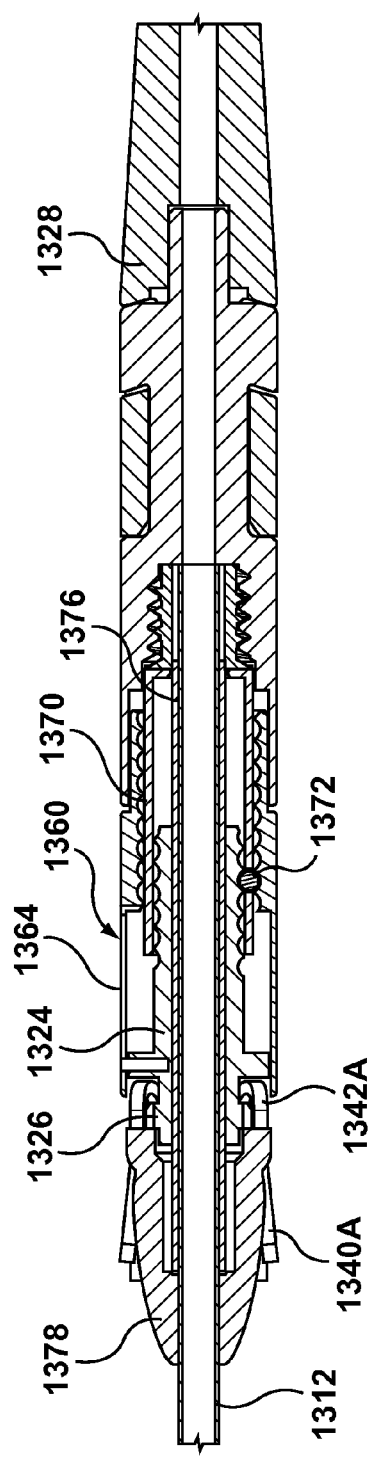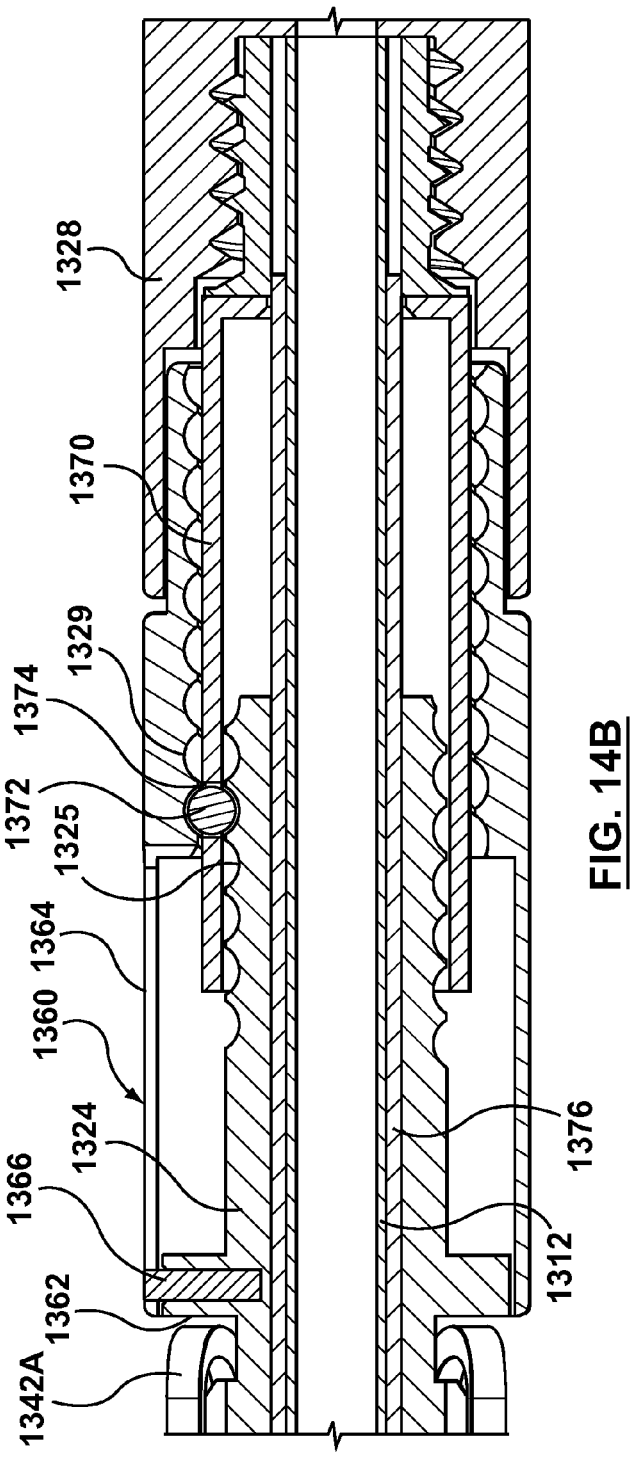

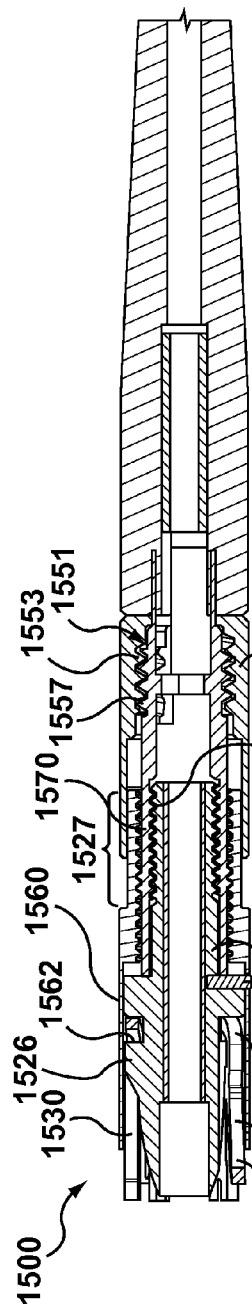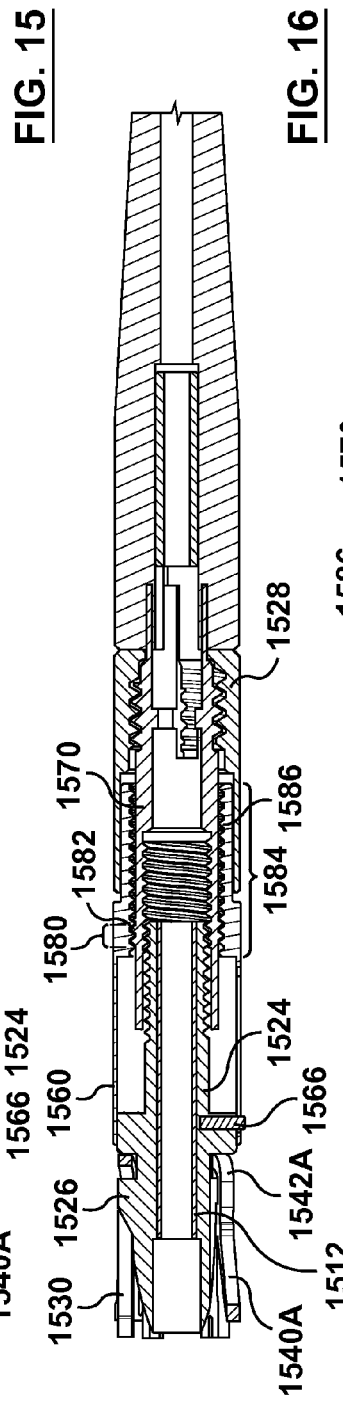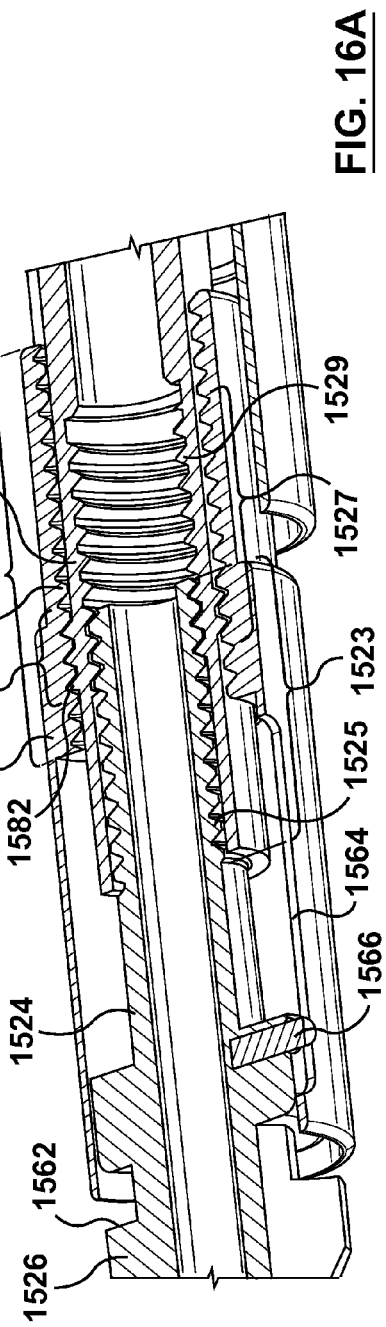

STENT-GRAFT DELIVERY SYSTEM HAVING A ROTATABLE SINGLE SHAFT TIP CAPTURE MECHANISM

FIELD OF THE INVENTION

The invention is related in general to implantable prostheses and in particular to self-expanding stent-grafts.

BACKGROUND OF THE INVENTION

Prostheses for implantation in blood vessels or other similar organs of the living body are, in general, well known in the medical art. For example, prosthetic vascular grafts constructed of biocompatible materials have been employed to replace or bypass damaged or occluded natural blood vessels. In general, endovascular grafts typically include a graft anchoring component that operates to hold a tubular graft component of a suitable graft material in its intended position within the blood vessel. Most commonly, the graft anchoring component is one or more radially compressible stents that are radially expanded in situ to anchor the tubular graft component to the wall of a blood vessel or anatomical conduit. Thus, endovascular grafts are typically held in place by mechanical engagement and friction due to the opposition forces provided by the radially expandable stents.

Grafting procedures are also known for treating aneurysms. Aneurysms result from weak, thinned blood vessel walls that "balloon" or expand due to aging, disease and/or blood pressure in the vessel. Consequently, aneurysmal vessels have a potential to rupture, causing internal bleeding and potentially life threatening conditions. Grafts are often used to isolate aneurysms or other blood vessel abnormalities from normal blood pressure, reducing pressure on the weakened vessel wall and reducing the chance of vessel rupture. As such, a tubular endovascular graft may be placed within the aneurysmal blood vessel to create a new flow path and an artificial flow conduit through the aneurysm, thereby reducing if not nearly eliminating the exertion of blood pressure on the aneurysm.

In general, rather than performing an open surgical procedure to implant a bypass graft that may be traumatic and invasive, endovascular grafts which may be referred to as stent-grafts are preferably deployed through a less invasive intraluminal delivery procedure. More particularly, a lumen or vasculature is accessed percutaneously at a convenient and less traumatic entry point, and the stent-graft is routed through the vasculature to the site where the prosthesis is to be deployed. Intraluminal deployment is typically effected using a delivery catheter with coaxial inner and outer tubes arranged for relative axial movement. For example, a self-expanding stent-graft may be compressed and disposed within the distal end of an outer catheter tube distal of a stop fixed to the inner member. The catheter is then maneuvered, typically routed through a body lumen until the end of the catheter and the stent-graft are positioned at the intended treatment site. The stop on the inner member is then held stationary while the outer tube of the delivery catheter is withdrawn. The stop prevents the stent-graft from being withdrawn with the sheath. As the sheath is withdrawn, the stent-graft is released from the confines of the sheath and radially self-expands so that at least a portion of it contacts and substantially conforms to a portion of the surrounding interior of the lumen, e.g., the blood vessel wall or anatomical conduit.

In recent years, to improve optimal control and alignment during deployment and positioning of a stent-graft, various tip capture spindles have been incorporated into the delivery system utilized for percutaneously delivering the stent-graft prosthesis. Tip capture involves restraining the proximal end stent of the stent-graft in a radially compressed configuration in conjunction with the main body restraint achieved by other delivery system components, such as a tubular cover shaft or sheath. The tip capture spindle can be activated at any time during stent-graft deployment to suit any number of system characteristics driven by the therapy type, stent-graft type, or specific anatomical conditions that may prescribe the release timing. Typically, the tip capture release is activated after some or all the main stent-graft body release, and thus provides a mean of restraining the stent-graft during positioning and any re-positioning. Additional restraint of the stent-graft is a key characteristic when the operator is attempting to accurately position the stent relative to an anatomical target. The tip capture restraint also aids in reducing an abrupt force of expansion when the stent-graft is released from the graft cover or sheath.

For example, U.S. Patent Application Publication No. 2006/0276872 to Arbefuielle et al. and U.S. Patent Application Publication No. 2009/0276027 to Glynn et al., both herein incorporated by reference in their entirety, describe tip capture mechanisms that restrain the proximal end stent of the stent-graft while the remainder of the stent-graft expands, then releases the proximal end stent. The proximal end stent (sometimes also referred to as the anchor stent) is attached to the graft material of the stent-graft so as to have an "open web" or "free flow" proximal end configuration in which the proximal endmost crowns thereof extend past or beyond the graft material such that the proximal endmost crowns are exposed or bare, and thus free to interact with a tip capture mechanism and couple the stent-graft prosthesis to the delivery system. FIGS. 1A and 1B illustrate a delivery system 10 having a tip capture spindle 12 designed to couple or interact with a stent-graft 14 having an open web or free flow proximal end configuration 16. More particularly, endmost crowns 18 engage or hook around retractable arms or retainer elements 20 of the tip capture spindle 12. Delivery system 10 includes at least three concentric shafts, namely an outer delivery sheath or graft cover 22, an intermediate shaft 24 coupled to tip capture spindle 12, and an elongate inner shaft 26 coupled to distal tip assembly 28. When graft cover 22 is retracted to allow stent-graft 14 to self-expand, endmost crowns 18 of the end stent 15 remain hooked around tip capture retainer elements 20, as shown in FIG. 1A. To release end stent 15, intermediate shaft 24 coupled to tip capture spindle 12 is retracted longitudinally relative to inner shaft 26 to retract tip capture spindle 12 such that end stent 15 is released from tip capture spindle 12 and allowed to self-expand, as shown in FIG. 1B. The Captivia Delivery System manufactured by Medtronic Vascular, Inc. of Santa Rosa, Calif. is one example of a delivery system having a tip capture mechanism as described above, which may be utilized for delivering endovascular stent-grafts such as the Valiant Thoracic Stent-graft manufactured by Medtronic Vascular, Inc. of Santa Rosa, Calif.

Tip capture mechanisms have improved accuracy of deployment of self-expanding stent-grafts. However, tip capture mechanisms known in the art require two or more concentric shafts, in addition to the outer sheath, such as intermediate shaft 24 and elongate inner shaft 26 described above with respect to FIG. 1 to retract the tip capture spindle and fully deploy the stent-graft. Two or more concentric shafts within the delivery system may cause several trackability and deployment challenges. More particularly, two or more concentric shafts increase the delivery or crossing profile of the delivery system. In addition, release forces associated with a delivery system having two or more concentric shafts that slide longitudinally relative to each other are relatively higher than a delivery system not requiring two or more concentric shafts because frictional forces between the two concentric shafts must be overcome to release the stent-graft from the tip capture spindle. Further, premature release of the stent-graft may occur when a user is attempting to maneuver the delivery system during repositioning of the stent-graft. When positioning or repositioning the delivery system, the user must push or pull the delivery system longitudinally. Due to the force required to push or pull the delivery system through tortuous vessels, the concentric shafts 24, 26 of the tip capture system may slide relative to each other, thereby causing premature release of the stent-graft from the tip capture spindle. Embodiments hereof relate to a delivery system having a tip capture mechanism to allow for partial deployment and repositioning of the stent-graft, wherein the delivery system more efficiently retracts the tip capture spindle.

BRIEF SUMMARY OF THE INVENTION

Embodiments hereof relate to a stent-graft delivery system including an elongate shaft, a tip capture spindle disposed over the shaft, a distal tip assembly coupled to the distal end of the shaft, and a stent-graft prosthesis mounted over the shaft. The stent graft prosthesis includes a stent coupled to a tubular graft. The tip capture spindle includes a plurality of retainer elements engaged with the stent of a stent-graft prosthesis. At least one component of the stent-graft delivery system constrains the stent engaged with the tip capture spindle into a delivery configuration and/or a partially-deployed configuration, and rotation of the elongate shaft results in longitudinal movement of the at least one component to release the stent from the tip capture spindle into a fully deployed configuration.

Embodiments hereof also relate to a stent-graft delivery system including an elongate shaft, a tip capture spindle disposed over the shaft, proximate to a distal end of the shaft, and a distal tip assembly coupled to the distal end of the shaft. A proximal portion of the tip capture spindle includes a plurality of retainer elements configured to engage a stent of a stent-graft prosthesis and a distal portion of the tip capture spindle includes threads on an outer surface thereof. A portion of the distal tip assembly proximally extends over the outer surface of the distal portion of the tip capture spindle and an inner surface of the proximally-extending portion of the distal tip assembly includes threads that mate with the threads on the tip capture spindle. Rotation of the elongate shaft rotates the distal tip assembly and results in longitudinal movement of the tip capture spindle.

Embodiments hereof also relate to a method of deploying a stent-graft prosthesis. A stent-graft delivery system is percutaneously advanced. The delivery system has a stent-graft prosthesis mounted on an elongate shaft, wherein a tip capture spindle is disposed over the shaft and a proximal portion of the tip capture spindle includes a plurality of retainer elements engaged with a stent of the stent-graft prosthesis. A distal tip assembly is coupled to a distal end of the shaft and a portion of the distal tip assembly proximally extends over an outer surface of a distal portion of the tip capture spindle. An inner surface of the distal tip assembly includes threads that mate with threads formed on the outer surface of the distal portion of the tip capture spindle. The stent-graft prosthesis is positioned and is partially deployed by retracting an outer sheath of the delivery system to expose the stent-graft prosthesis, wherein the stent-graft prosthesis self-expands and the stent remains engaged with the plurality of retainer elements of the tip capture spindle. The elongate shaft is rotated to fully deploy the stent-graft prosthesis, wherein rotation of the elongate shaft rotates the distal tip assembly and results in longitudinal movement of the tip capture spindle.

Embodiments hereof also relate to a stent-graft delivery system including an elongate shaft, a tip capture spindle disposed over the shaft, proximate to a distal end of the shaft, and a distal tip assembly coupled to the distal end of the shaft. The tip capture spindle includes a plurality of retainer elements configured to engage a stent of a stent-graft prosthesis. A portion of the distal tip assembly proximally extends over elongate shaft and an outer surface of the distal tip assembly includes threads. A sleeve extends over the retainer elements of the tip capture spindle to the distal tip assembly. An inner surface of the sleeve includes threads that mates with the threads on outer surface of the distal tip assembly, and rotation of the elongate shaft rotates the distal tip assembly and results in longitudinal movement of the sleeve.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 7 is a perspective view of a distal portion of a stent-graft delivery system having a single elongate shaft for a tip capture mechanism according to another embodiment hereof, wherein a stent-graft prosthesis mounted on the delivery system has a closed-web proximal end configuration and is in a delivery or partially-deployed configuration.

FIG. 7A is a cross-sectional view of FIG. 7.

FIG. 8 is a proximal end view taken along line A-A of FIG. 7.

FIG. 9 is an enlarged sectional perspective view of a portion of FIG. 7.

FIG. 10 is a perspective view of a distal portion of the stent-graft delivery system of FIG. 7, wherein the stent-graft prosthesis is in a fully deployed configuration.

FIG. 10A is a cross-sectional view of FIG. 10.

FIG. 11 is a perspective view of a distal portion of a stent-graft delivery system having a single elongate shaft for a tip capture mechanism according to another embodiment hereof, wherein a barbed stent-graft prosthesis mounted on the delivery system is in a delivery or partially-deployed configuration.

FIG. 11A is a cross-sectional view of FIG. 11.

FIG. 11B is an enlarged view of a portion of FIG. 11A.

FIG. 13 is a perspective view of a distal portion of a stent-graft delivery system having a single elongate shaft for a tip capture mechanism according to another embodiment hereof, wherein a barbed stent-graft prosthesis mounted on the delivery system is in a delivery or partially-deployed configuration and the delivery system includes two components that are moved in opposing longitudinal directions during deployment of the stent-graft prosthesis.

FIG. 13A is a cross-sectional view of FIG. 13.

FIG. 13B is an enlarged view of a portion of FIG. 13A.

FIG. 14A is a cross-sectional view of the distal portion of the stent-graft delivery system of FIG. 13, wherein the stent-graft prosthesis is in a fully deployed configuration.

FIG. 14B is an enlarged view of a portion of FIG. 14A.

FIG. 15 is a cross-sectional view of a distal portion of a stent-graft delivery system having a single elongate shaft for a tip capture mechanism according to another embodiment hereof, wherein a barbed stent-graft prosthesis mounted on the delivery system is in a delivery or partially-deployed configuration and the delivery system includes two components in a double threaded relationship that are moved in opposing longitudinal directions during deployment of the stent-graft prosthesis.

FIG. 16 is a cross-sectional view of the distal portion of the stent-graft delivery system of FIG. 15, wherein the stent-graft prosthesis is in a fully deployed configuration.

FIG. 16A is an enlarged perspective view of a portion of FIG. 16, wherein the stent-graft prosthesis and the elongate shaft of the delivery shaft have been omitted for clarity.

DETAILED DESCRIPTION OF THE INVENTION

Figure 1A:
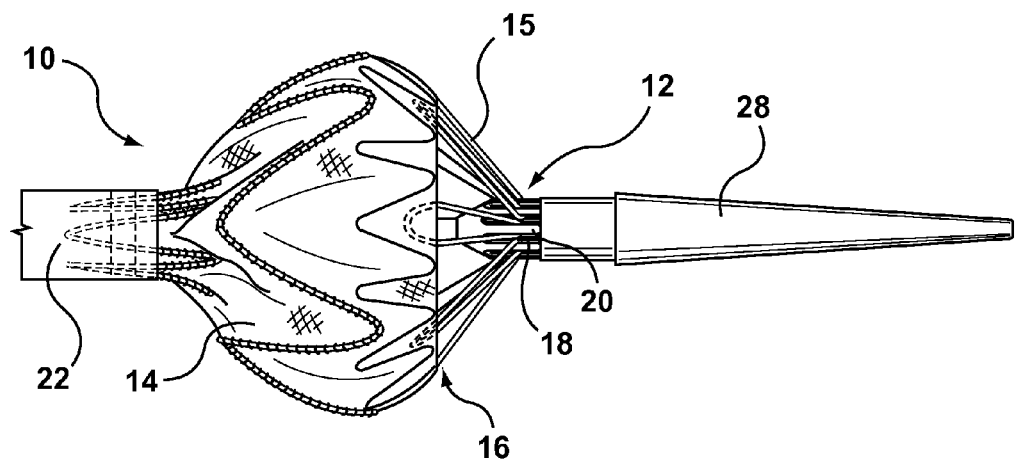
FIGS. 1A and 1B are side views of a distal end of a delivery system having a tip capture spindle designed to couple or interact with a stent-graft having an open web or free flow proximal end configuration.
Figure 1B:
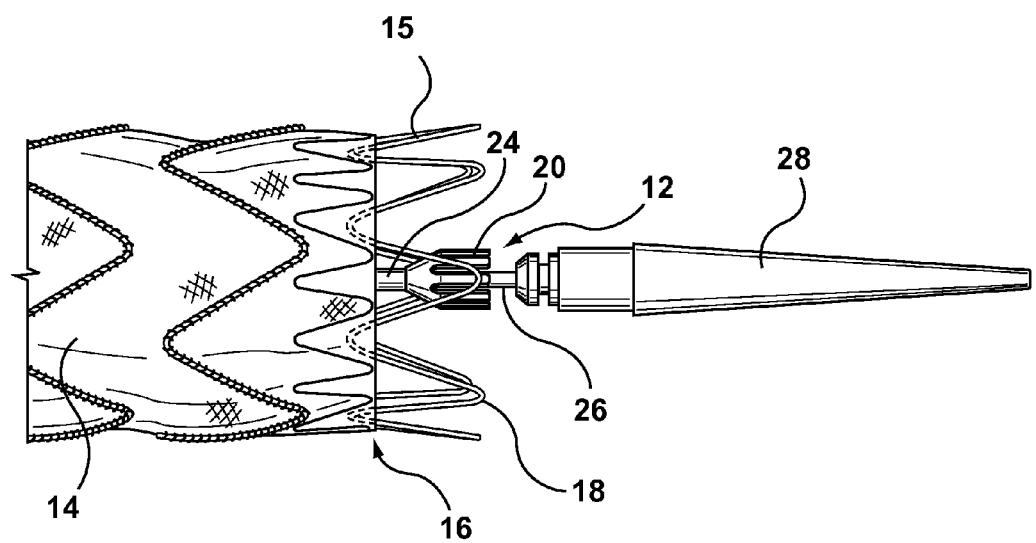

Specific embodiments of the present invention are now described with reference to the figures, wherein like reference numbers indicate identical or functionally similar elements. Specific embodiments are now described with reference to the figures, wherein like reference numbers indicate identical or functionally similar elements. Unless otherwise indicated, for the delivery system the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. For the stent-graft prosthesis "proximal" is the portion nearer the heart by way of blood flow path while "distal" is the portion of the stent-graft further from the heart by way of blood flow path. In addition, the term "self-expanding" is used in the following description with reference to one or more stent structures of the prostheses hereof and is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

The following detailed description is merely exemplary in nature and is not intended to limit the invention or the application and uses of the invention. Although the description of the invention is in the context of treatment of blood vessels such as the aorta, coronary, carotid and renal arteries, the invention may also be used in any other body passageways where it is deemed useful. Furthermore, there is no intention to be bound by any expressed or implied theory presented in the preceding technical field, background, brief summary or the following detailed description.

Embodiments hereof relate to stent-graft delivery systems having a tip capture mechanism that allows for partial deployment and repositioning of the stent-graft prosthesis. Rather than retraction of an intermediate or outer shaft over an inner shaft for final deployment of the stent-graft prosthesis as required in prior delivery systems described above, a single elongate shaft is rotated for final deployment or tip release of the stent-graft prosthesis. In embodiments hereof, as will be explained in more detail below, a tip capture spindle which holds or retains an end stent of the stent-graft prosthesis is in a threaded relationship with a distal tip assembly of the delivery system. The distal tip assembly is coupled or attached to the single elongate shaft such that rotation of the shaft also rotates the distal tip assembly. When the elongate shaft and distal tip assembly are rotated, the rotational movement is converted to translational or linear movement of the tip capture spindle due to the threaded relationship between the spindle and the distal tip assembly. As a result, the tip capture spindle may be longitudinally driven back or forth to release the end stent for final deployment of the stent-graft prosthesis. Release forces are thus improved due to the mechanical advantage of threads used to convert rotational movement of the shaft into translational movement of the tip capture spindle. The rotational forces to rotate the single shaft and thereby actuate tip release are significantly less than forces required to move or retract an intermediate shaft over an inner shaft in the prior systems described above. More particularly, when being tracked through a vasculature, the shaft(s) of a delivery system take on the shape of the vascular system and frictional issues may arise. If the delivery system includes concentric intermediate and inner shafts as in the prior systems described above, the shafts move within one another along their shared axis and the frictional elements that occur at every node or turn of tortuosity are additive and rapidly become significant. The required tensile limits of the concentric shafts result in an increased wall thickness of the shafts, thus reducing useful cross sectional area of the delivery system profile. On the other hand, if a shaft of the delivery system turns or rotates around its longitudinal axis, the torque transmitted through the shaft to actuate the tip capture is modest or minimal. The polar moment of inertia necessary to turn/rotate the shaft is also low and is not affected by tortuosity. Accordingly, in embodiments hereof in which only a single elongate shaft is rotated, the elongate intermediate or outer shaft eliminated and the required tensile limits of the single elongate shaft do not result in an increased wall thickness, thereby minimizing the wall thickness and material requirements of the rotatable shaft.

Figure 2:
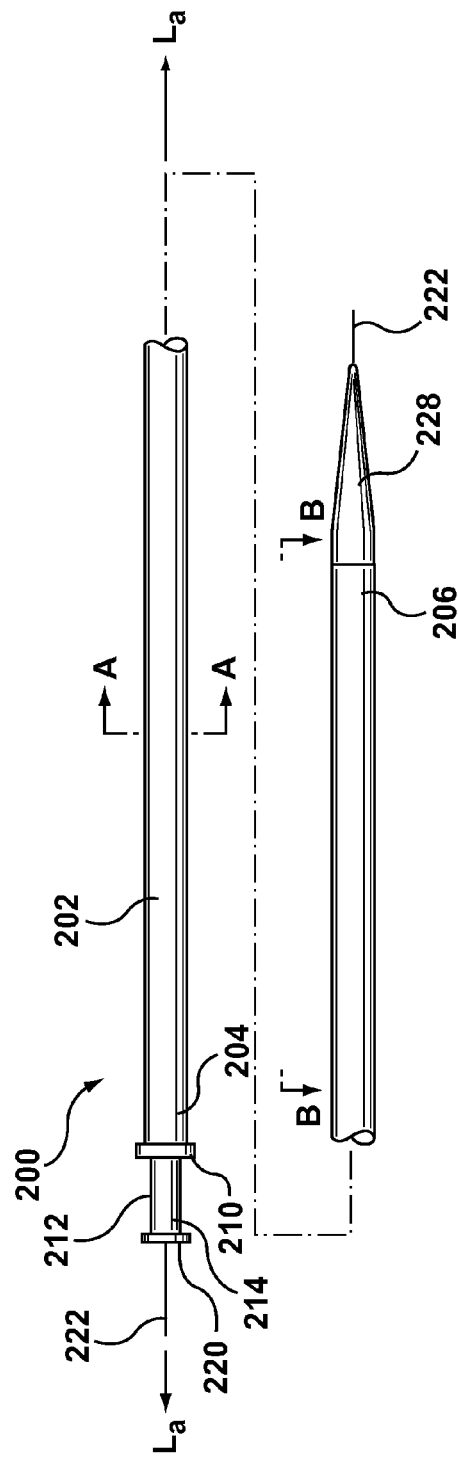
FIG. 2 is a side view of a stent-graft delivery system having a single elongate shaft for a tip capture mechanism according to an embodiment hereof, wherein a stent-graft prosthesis mounted on the delivery system is in a delivery configuration.
Figure 2B:
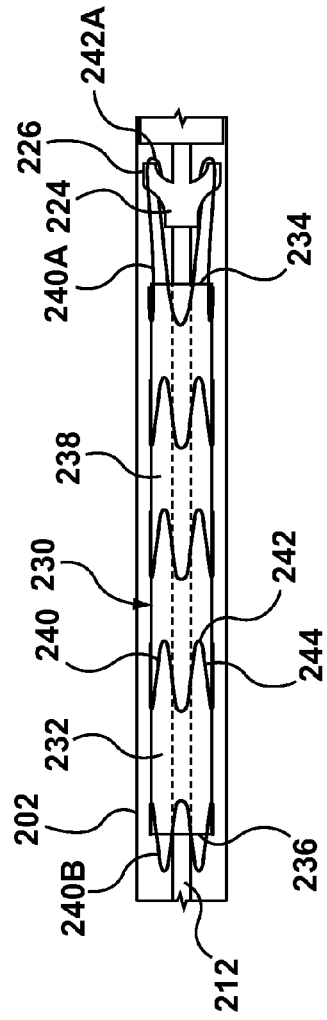
FIG. 2B is a cross-sectional view taken along the line B-B of FIG. 2.
Figure 2A:
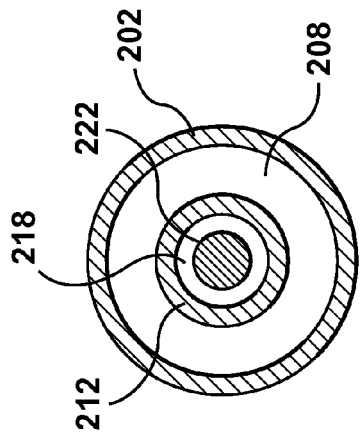
FIG. 2A is a cross-sectional view taken along the line A-A of FIG. 2.
Figure 3:
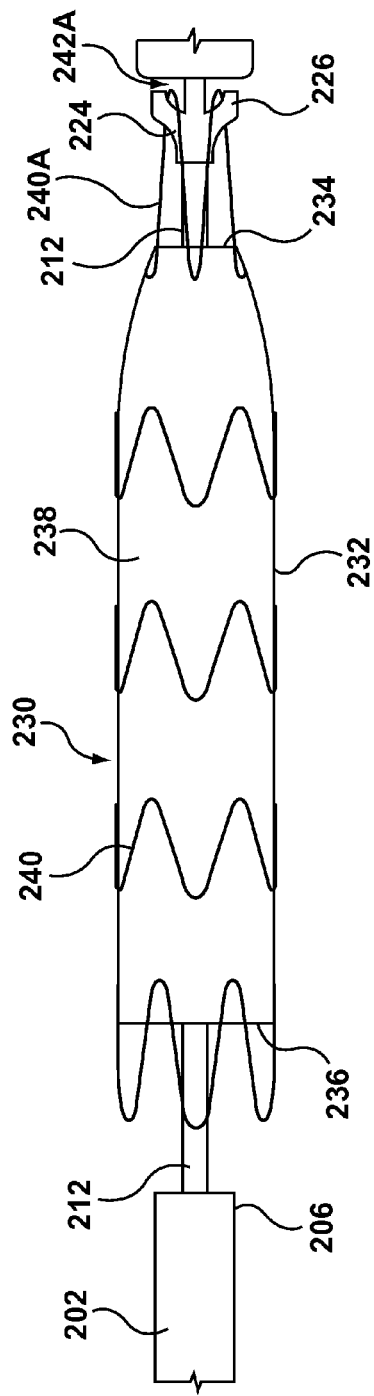
FIG. 3 is a side view of a distal portion of the stent-graft delivery system of FIG. 2, wherein the stent-graft is in a partially deployed configuration.
Figure 5:
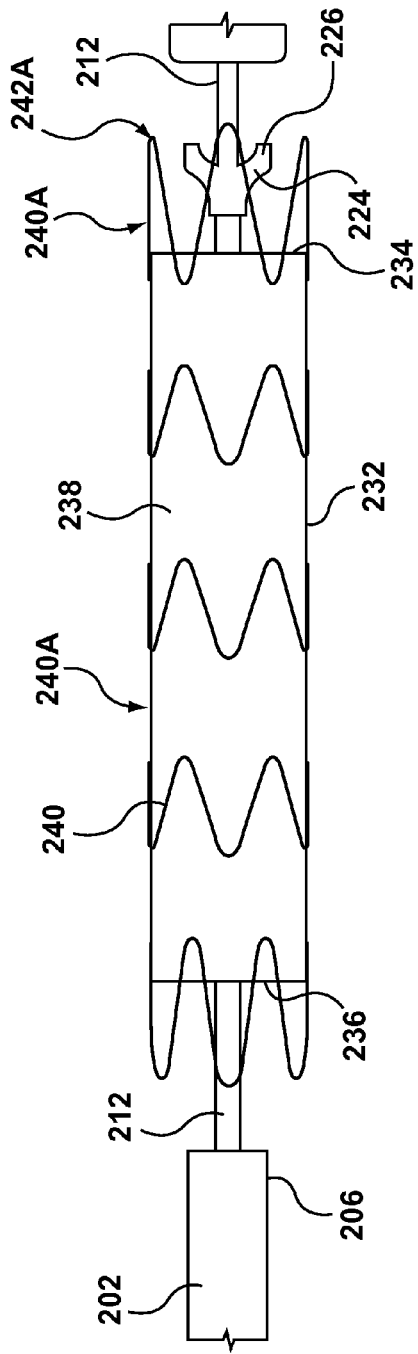
FIG. 5 is a side view of a distal portion of the stent-graft delivery system of FIG. 2, wherein the stent-graft is in a fully deployed configuration.
Figure 4:
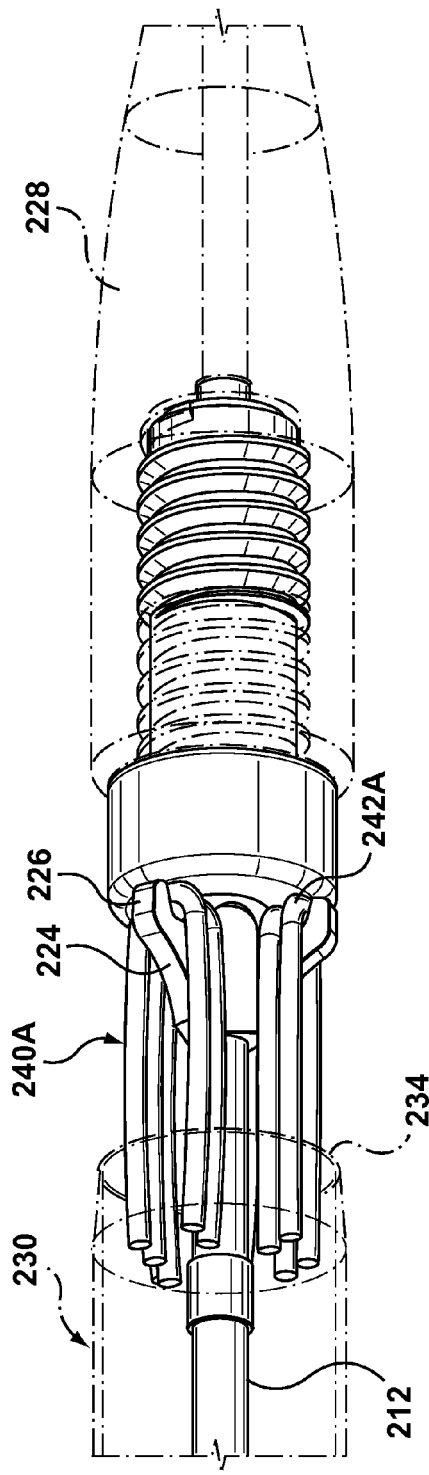
FIG. 4 is a perspective view of a distal portion of the stent-graft delivery system of FIG. 2, wherein the stent-graft is in a partially deployed configuration.
Figure 6:
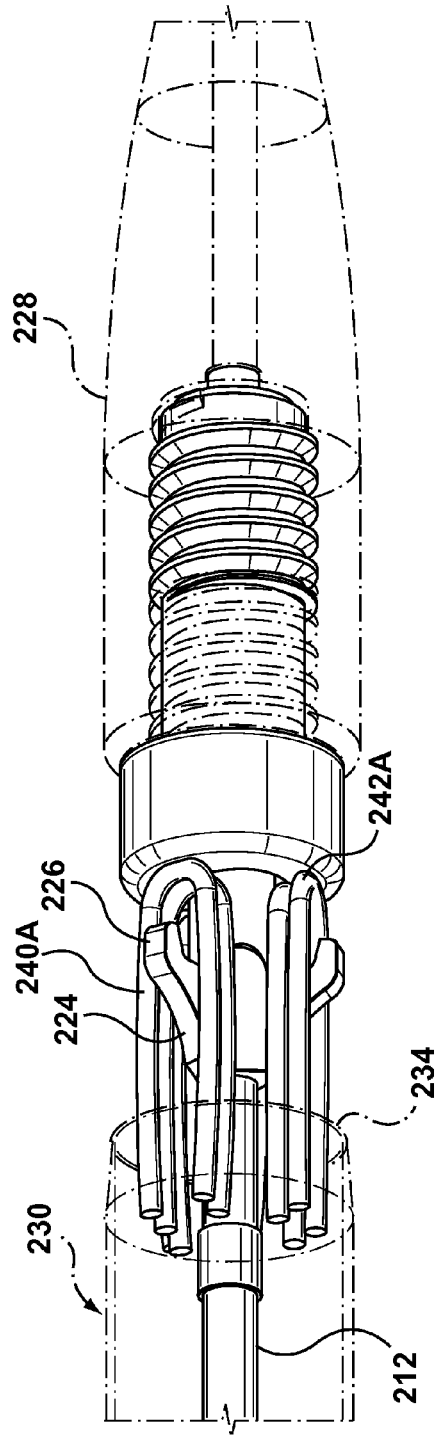
FIG. 6 is a perspective view of a distal portion of the stent-graft delivery system of FIG. 2, wherein the stent-graft is in a fully deployed configuration.

According to an embodiment hereof, a delivery system 200 having a tip capture mechanism to allow for partial deployment and repositioning of the stent-graft is shown and described with respect to FIGS. 2-6. FIGS. 2, 2A, and 2B illustrate delivery system 200 for delivering a self-expanding stent-graft prosthesis 230 within a vasculature, wherein stent-graft prosthesis 230 is in a compressed delivery configuration. FIG. 2 is a schematic side view of system 200, while FIG. 2A is a cross-sectional view taken along line A-A of FIG. 2 and FIG. 2B is a sectional view taken along line B-B of FIG. 2. FIGS. 3 and 4 illustrate a distal portion of delivery system 200 in a partially deployed configuration, and FIGS. 5 and 6 illustrate a distal portion of delivery system 200 in a deployed configuration. In FIG. 6, stent-graft prosthesis 230 is still shown with first end stent 240A undeployed for convenience of seeing the relationship between the stent-graft 230 and the delivery system 200, but it would be understood by those having ordinary skill in the art that once tip capture spindle 224 is retracted such that crowns 242A of first end stent 240A are not retained by spindle 224, first end stent 240A will self-expand to fully deploy stent graft prosthesis 230, as described in more detail below.

Figure 6A:
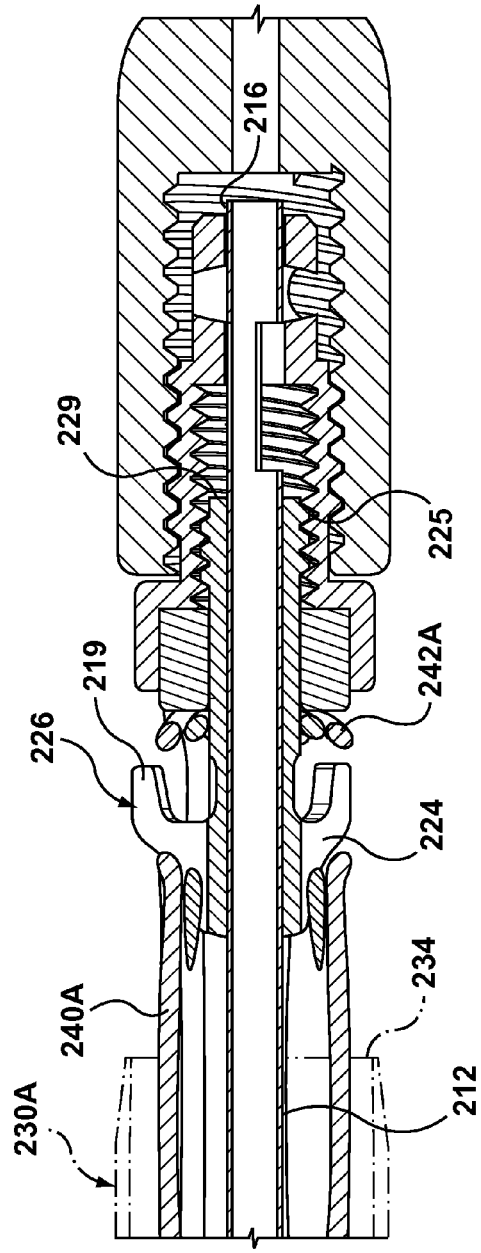
FIG. 6A is a cross-sectional view of FIG. 6.

Stent-graft delivery system 200 includes an elongate shaft 212 having a proximal end 214 and a distal end 216 (shown in cross-sectional views of FIGS. 4A and 6A), and a distal tip assembly 228 is coupled to distal end 216 of elongate shaft 212. Elongate shaft 212 may be constructed from a flexible metal tube of NiTi (Nitinol™), stainless steel, or the like, or may be constructed of a rigid plastic tube of PEEK polyetheretherketone, polyimide, or the like. Elongate shaft 212 may have any suitable working length, for example, 550 mm-600 mm, to extend to a target location where stent-graft 230 is to be implanted. Distal tip assembly 228 may be tapered and flexible to provide trackability through the vasculature. Those skilled in the art will appreciate that distal tip assembly 228 can be formed as a single unit and/or assembled from individual parts or components. Distal tip assembly 228 can be constructed by insert molding one or more components thereof over elongate shaft 212. Suitable materials for distal tip assembly 228 include Pebax, urethane, silicone, other flexible polymers, and the like, any of which may also include a radiopaque additive to provide the clinician with a visible tip when using fluoroscopy guidance to deliver the stent-graft within the patient. In an embodiment, elongate shaft 212 may define a guidewire lumen 218 for receiving a guidewire 222 there through. Elongate shaft 212 may be advanced over an indwelling guidewire to track the delivery system to the target site. Alternatively, elongate shaft 212 may instead be a solid rod (not shown) without a lumen extending there through. In an embodiment where elongate shaft 212 is a solid rod, elongate shaft 212 is tracked to the target site with the assistance of tapered distal tip assembly 228. In addition, delivery system 200 may include a radiopaque marker (not shown) allowing for accurate positioning of the delivery system prior to deployment of the stent-graft.

Stent-graft prosthesis 230 is disposed around elongate shaft 212, proximate to distal end 216 thereof. Stent-graft prosthesis 230 includes a tubular graft 232 having a first edge or end 234, a second edge or end 236, and a body 238 there between which defines a lumen (not shown) through stent-graft prosthesis 230. In an embodiment, first end 234 of graft 232 may be referred to as a proximal end of graft 232 and a proximal end of stent-graft prosthesis 230, which is conventionally the end that is coupled to a tip capture mechanism of a delivery system, and second end 236 of graft 232 may be referred to as a distal end of graft 236 and a distal end of stent-graft prosthesis 230. Graft 232 may be formed from any suitable graft material, for example and not limited to, a low-porosity woven or knit polyester, DACRON material, expanded polytetrafluoroethylene, polyurethane, silicone, or other suitable materials. In another embodiment, the graft material could also be a natural material such as pericardium or another membranous tissue such as intestinal submucosa. Stent-graft prosthesis 230 also includes at least one radially-compressible stent or scaffold 240 that is coupled to graft 232 for supporting the graft material and that is operable to self-expand into apposition with an interior wall of a body vessel (not shown). In the embodiment depicted in FIG. 2B, stent-graft prosthesis 230 includes a series of five independent or separate cylindrical stents 240. Each stent 240 is constructed from a self-expanding or spring material, such as Nitinol, and is a sinusoidal patterned ring including a plurality of crowns or bends 242 and a plurality of struts or straight segments 244 with each crown being formed between a pair of opposing struts. Although shown with five stents 240, it will be understood by those of ordinary skill in the art that stent-graft prosthesis 230 may include a greater or smaller number of stents 240 depending upon the desired length of stent-graft prosthesis 230 and/or the intended application thereof. For description purposes only, the stent that is coupled adjacent and proximate to first end 234 of graft 232 is referred to herein as first end stent 240A and the stent that is coupled adjacent and proximate to second end 236 of graft 232 is referred to herein as second end stent 240B but it will be understood by those of ordinary skill in the art that all of the stents may have identical or different patterns or configurations. Stents 240 are coupled to graft 232 by stitches or other means known to those of skill in the art. In the embodiment shown in FIG. 2, stents 240 are coupled to an outer surface of graft 232. However, stents 240 may alternatively be coupled to an inside surface of graft 232. When stent-graft prosthesis 230 is used for treating an aneurysm, stents 240 have sufficient radial spring force and flexibility to conformingly engage stent-graft prosthesis 230 with the body lumen inner wall, to avoid excessive leakage, and prevent pressurization of the aneurysm, i.e., to provide a leak-resistant seal. Although some leakage of blood or other body fluid may occur into the aneurysm isolated by stent-graft prosthesis 230, an optimal seal will reduce the chances of aneurysm pressurization and resulting rupture.

Figure 4A:
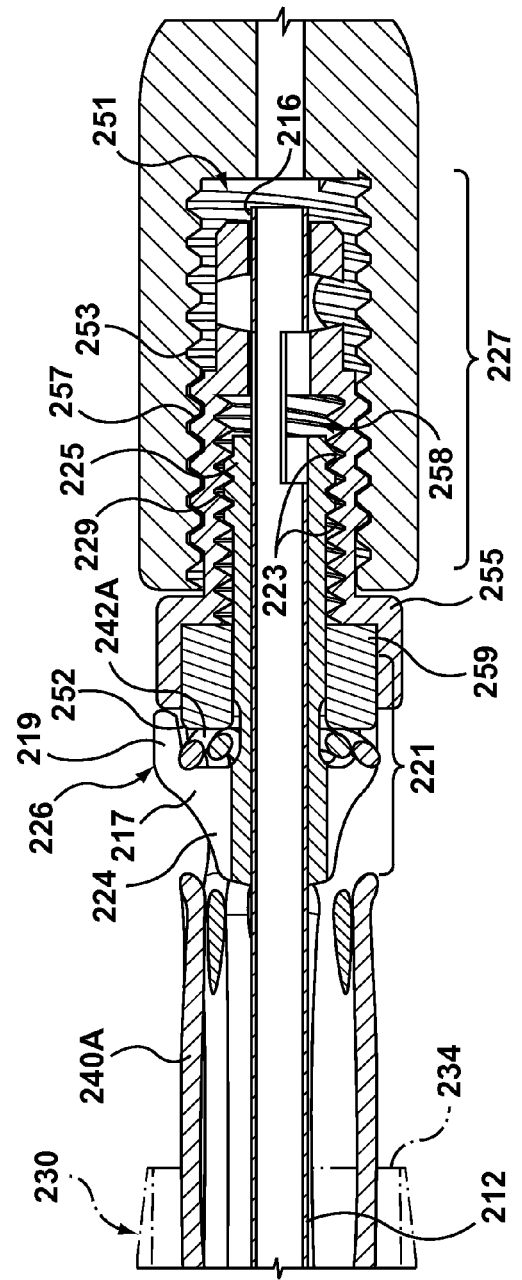
FIG. 4A is a cross-sectional view of FIG. 4.

In the embodiment of FIGS. 2-6, stent-graft 230 has an open-web or free-flow proximal end configuration. The open web proximal end configuration allows blood flow through endmost crowns 242A for perfusion during and/or after implantation. As utilized herein, "endmost crowns" refers to the most proximal crowns or peaks of the stent-graft prosthesis, regardless of whether or not the crowns are coupled to the graft material or whether the crowns extend beyond the edge of the graft material. More particularly, first end stent 240A is attached to graft 232 so that endmost crowns 242A thereof extend past or beyond the graft material such that the endmost crowns are exposed or bare, and thus free to interact with a tip capture spindle 224 and couple stent-graft prosthesis 230 to delivery system 200. Tip capture spindle 224 functions to retain or hold first end 234 of stent-graft prosthesis 230 during delivery. Tip capture spindle 224 is disposed around elongate shaft 212 and is rotatable relative to shaft 212. In the delivery configuration shown in FIG. 2B endmost crowns 242A of first end stent 240A engage or hook around retainer elements 226 of tip capture spindle 224. Retainer elements 226 are formed on a proximal portion 221 of tip capture spindle 224, as best shown in FIG. 4A. In the embodiment of FIGS. 2-6, retainer elements 226 are disposed around the circumference of tip capture spindle 224 and each retainer element 226 includes a radially-extending base segment 217 and an arm segment 219 that extends distally from base segment 217 such that arm segment 219 is spaced apart from an outer surface of elongate shaft 212 to define a recess 252 that receives one or more endmost crowns 242A. When endmost crowns 242A are received within recesses 252, arm segments 219 of retainer elements 226 distally and longitudinally extend over and cover endmost crowns 242A to retain the crowns in a delivery configuration. Arm segments 219 of retainer elements 226 of tip capture spindle 224 can be substantially parallel to the central or longitudinal axis of elongate shaft 212, i.e., the longitudinal axis of delivery system 200. In other embodiments, retainer elements 226 can curve toward or away from the longitudinal axis of delivery system 200 as desired for a particular purpose. In an embodiment, the number of retainer elements 226 of tip capture spindle 224 is equal to half the number of endmost crowns 242A of first end stent 240A and two endmost crowns are received in each recess 252, as best shown in FIG. 4, in a piggyback or stacking manner to further reduce the effective diameter of the delivery system. Struts 240 of first end stent 240A are of equal length and two crowns 242A are stacked directly on top of one another within each recess 252. In another embodiment (not shown in FIGS. 2-6), the number of retainer elements 226 of tip capture spindle 224 is equal to the number of endmost crowns 242A of first end stent 240A and one endmost crown is received in each recess.

Stent-graft delivery system 200 also includes a retractable outer sheath or graft cover 202 to contain stent-graft prosthesis 230 in a constrained diameter configuration while the graft delivery system is tracked through a body lumen to the deployment site. Graft cover 202 may be constructed of any suitable flexible polymeric material, including but not limited to polyethylene terephalate (PET), nylon, polyethylene, PEBAX, or combinations thereof, either blended or co-extruded. In FIG. 2, graft cover 202 is in a non-retracted, delivery configuration. Graft cover 202 defines a lumen 208 extending from a proximal end 204 to a distal end 206, and elongate shaft 212 slidably extends through lumen 208 of graft cover 202. Graft cover 202 is movable in an axial direction along and relative to elongate shaft 212 and extends to a proximal portion of the graft delivery system where it may be controlled via an actuator, such as a handle 210 to selectively expand the graft disposed around distal end 216 of elongate shaft 212. Handle 210 may be a push-pull actuator that is attached or connected to proximal end 204 of graft cover 202. Alternatively, the actuator may be a rotatable knob (not shown) that is attached or connected to proximal end 204 of graft cover 202 such that when the knob is rotated, graft cover 202 is retracted in a proximal direction to expand the graft. Thus, when the actuator is operated, i.e., manually turned or pulled, graft cover 202 is proximally retracted over elongate shaft 212 in a proximal direction.

When initial or partial deployment of prosthesis 230 is desired, graft cover 202 is retracted to allow body 238 of prosthesis 230 to self-expand. As shown in FIGS. 3-4, when stent-graft prosthesis 230 is in a partially deployed configuration, endmost crowns 242A of first end stent 240A remain hooked around tip capture spindle 224. Notably, stent-graft prosthesis 230 is still coupled to delivery system 200 if repositioning of the stent-graft 230 is required. In the embodiment depicted in FIG. 3, graft cover 202 is retracted such that a distal end thereof no longer covers or constrains distal or second end 236 of prosthesis 230, thereby allowing distal or second end 236 of prosthesis 230 to self-expand and deploy. In another embodiment hereof (not shown), graft cover 202 is retracted such that a distal end thereof remains over and radially constrains a distal or second end 236 of prosthesis 230 in order to eliminate or minimize any inclination of prosthesis 230 to rotate/spin when elongate shaft 212 is rotated as further described herein.

After any repositioning is performed and stent-graft prosthesis 230 is positioned as desired, stent-graft prosthesis 230 may be fully deployed and released from delivery system 200 by rotating or turning elongate shaft 212 to retract tip capture spindle 224. Tip capture retainer elements 226 are retracted until arm segments 219 no longer cover endmost crowns 242A of first end stent 240A, thereby permitting first end stent 240A to fully expand or deploy as shown in FIG. 5-6. More particularly, spindle 224 is disposed around and rotatable relative to elongate shaft 212, and is coupled to distal tip assembly 228 via a threaded connection. Spindle 224 is also slideable relative to shaft 212. In particular, as shown in FIGS. 4, 4A, 6, and 6A, a proximal portion 227 of distal tip assembly 228 includes a recess or bore 251. The bore 251 includes female or internal threads 253. An insert 255 is disposed in bore 251 and includes external or male threads 257 to interlock with threads 253. Insert 255 in this embodiment is locked within bore 251 and is considered part of distal tip assembly 228. As would be understood by those of ordinary skill in the art, insert 255 may be connected to the remainder of distal tip assembly 228 by other means, such as adhesives or other mechanical connectors, or may be unitary with the remainder of distal tip assembly 228. Insert 255 also includes a bore 258 there within including internal or female threads 229. A distal portion 223 of spindle 224 includes male or external threads 225 to mate with threads 229 to convert rotational movement into translational or linear movement. Threads 225, 229 are continuous helical ridges that wrap around an outer surface of spindle 224 and an inner surface of insert 255, respectively, to form a matched or mating pairs of threads. As will be understood by those of ordinary skill in the art, threads 225, 229 are used to convert rotational to translational or linear movement. Distal tip assembly 228 also includes a spacer 259 disposed within a recess or pocket at a proximal end of insert 255. Spacer 259 is formed from an elastomer material such as rubber, and functions to push and secure endmost crowns 242A of stent-graft 230 within recesses 252 defined by retainer elements 226 when crowns 242A are captured by distal tip spindle 224 in the delivery configuration, as shown in FIG. 4A. Endmost crowns 242A of stent-graft 230 are essentially wedged or sandwiched between spacer 259 and radially-extending base segments 217 of retainer elements 226 to prevent premature release of end stent 240A that may otherwise occur if endmost crowns 242A are not pushed against radially-extending base segments 217 of retainer elements 226. As would be recognized by those skilled in the art, spacer 259 may be integral with insert 255, which may be integral with the remainder of distal tip assembly 228.

In order to move distal tip spindle 224 to release endmost crowns 242A of stent-graft 230, shaft 212 is rotated. Shaft 212 is coupled to distal tip assembly 228 (including insert 255) such that rotation of shaft 212 causes rotation of distal tip assembly 228 (i.e., they are not rotatable relative to each other). When elongate shaft 212 is rotated, distal tip assembly 228 with insert 255 fixedly attached thereto is also rotated. Distal spindle 224 is prevented from rotation due to endmost crowns 242A of first end stent 240, which extend between adjacent retainer elements 226 of spindle 224. Because spindle 224 is prevented from rotating, rotation of elongate shaft 212 results relative rotation of spindle 224 and insert 255 along threads 225, 229, thereby causing the rotational movement to be converted to translational or linear movement between spindle 224 and tip assembly 228. Because the longitudinal location of shaft 212 and distal tip assembly is fixed at proximal end 214 of inner shaft 212 via a hub or locking component (not shown), spindle 224 is longitudinally driven back or forth along the main or longitudinal axis $L_A$ of delivery system 200. If elongate shaft 212 is rotated in a first direction, i.e. clockwise or counter-clockwise depending upon the direction of the threaded connection 225, 229 between spindle 224 and distal tip assembly 228, spindle 224 may be proximally retracted to disengage endmost crowns 242A of first end stent 240A from retainer elements 226 of spindle 226 for final deployment of stent-graft prosthesis 230. Elongate shaft 212 may be rotated via an actuator coupled to proximal end 214 thereof, such as a rotatable knob or handle 220.

After first end stent 240A is permitted to deploy and crowns 242A of first end stent 240A no longer extend between adjacent retainer elements 226 of spindle 224, continued rotation of elongate shaft 212 does not result in longitudinal movement of spindle 224 because spindle 224 is no longer prevented from rotation. Rather, continued rotation of elongate shaft 212 after first end stent 240A is deployed results in spinning/rotation of spindle 224.

A delivery system requiring with a tip capture mechanism as generally described above may also be utilized to deliver and deploy a stent-graft prosthesis having a proximal closed web configuration. In a closed web configuration, the endmost crowns do not extend past or beyond the graft material but rather are covered by graft material. Stent-grafts having a closed web proximal configuration do not have a bare proximal end stent free to interact with a tip capture spindle of a delivery system. In some cases a closed web configuration may be required or chosen due to application, i.e., a thoraric aortic aneurysm rather than an abdominal aortic aneurysm, and/or user preferences. For example, FIGS. 7-10 illustrate another embodiment hereof delivery system 700 having a tip capture mechanism to allow for partial deployment and repositioning of a self-expanding stent-graft prosthesis 730 which has a proximal closed web configuration. FIGS. 7, 7A, 8, and 9 illustrate a distal portion of delivery system 700 with stent-graft prosthesis 230 in either a delivery configuration or a partially deployed configuration, and FIG. 10 illustrates a distal portion of delivery system 700 with delivery system 700 in a deployed configuration. In FIG. 10, stent-graft prosthesis 730 is still shown with first end stent 740A undeployed for convenience of seeing the relationship between the stent-graft 730 and the delivery system 700, but it would be understood by those having ordinary skill in the art that once sutures 750 are released from spindle 724, first end stent 740A will self-expand to fully deploy stent-graft prosthesis 730, as described in more detail below. FIG. 7A is a cross-sectional view of FIG. 7, while FIG. 8 is an end view taken along line A-A of FIG. 7 and FIG. 9 is an enlarged sectional view of a portion of FIG. 7. Similar to delivery system 200, delivery system 700 has a reduced delivery or crossing profile compared to prior delivery systems and requires less force to move the tip capture mechanism for final deployment of stent-graft 730.

Delivery system 700 includes an elongate shaft 712 having a proximal end (not shown in FIGS. 7-10) and a distal end 716, and a tapered distal tip assembly 728 is coupled to distal end 716 of elongate shaft 712 such that distal tip assembly 728 does not rotate relative to shaft 712. Although not shown in FIGS. 7-10, stent-graft delivery system 700 also includes a retractable outer sheath or graft cover (not shown) to contain stent-graft prosthesis 730 in a constrained diameter configuration while the graft delivery system is tracked through a body lumen to the deployment site. Stent-graft prosthesis 730 is disposed around elongate shaft 712, proximate to distal end 716. Only a proximal portion of stent-graft prosthesis 730 is shown in FIGS. 7-10. Stent-graft prosthesis 730 is similar to stent-graft prosthesis 230, except that at least a first end 734 of stent-graft prosthesis 730 has a closed web configuration in which proximal endmost crowns 742A of a first end stent 740A are covered or lined by a tubular graft 732 and do not extend past or beyond first end 734 of graft 732.

Endmost crowns 742A of end stent 740A may be stitched or otherwise secured to graft 732 and thus are not free to interact with a tip capture spindle 724, which is also mounted on elongate shaft 712. Rather, in this embodiment, a plurality of suture loops 750 couple graft 732 to retainer elements 726 of tip capture spindle 724. In an embodiment, the number of suture loops 750 and the number of retainer elements 726 are equal to the number of endmost crowns 742A of first end stent 740A and a suture loop 750 couples graft 732 to a respective retainer element 726 adjacent to each endmost crown 742A. However, more or less suture loops and retainer elements may be used. Each suture loop 750 passes through the graft material of graft 732, and engages or hooks around a retainer element 726 of tip capture spindle 724. In an embodiment, as shown in FIG. 7A, each retainer element 726 of tip capture spindle 724 includes a recess or groove 752 formed on an inner surface thereof for receiving a suture loop 750. Each suture loop 750 may be captured between recess 752 of retainer 726 and elongate shaft 712. To ensure retention to the suture loop, elongate shaft 712 may include an enlarged portion 754 having an outer diameter greater than the outer diameter of the remainder of the shaft 712 and each suture loop 750 may be received within a recess 752 of retainer 726, adjacent to enlarged portion 754 of elongate shaft 712. Enlarged portion 754 may be formed by overmoulding material onto elongate shaft 712.

To fully deploy and release stent-graft prosthesis 730 from delivery system 700, elongate shaft 712 is rotated to distally advance tip capture spindle 724, thereby disengaging or removing retainer elements 726 of tip capture spindle 724 from suture loops 750 as shown in FIG. 10 such that first end stent 740A of stent-graft prosthesis 730 is permitted to fully expand or deploy. Similar to delivery system 200, spindle 724 is disposed around elongate shaft 712 such that spindle 724 may rotate and slide relative to shaft 712. Further, spindle 724 is coupled to distal tip assembly 728 via a threaded connection. A distal portion 723 of spindle 724 includes male or external threads 725, and a proximal portion 727 of distal tip assembly 728 includes a 251 with female or internal threads 729 on an inner surface defined by bore 751. In the embodiment shown in FIGS. 7-10, proximal portion 727 of distal tip assembly 728 is coupled to the remainder of the distal tip assembly by a lap connection 731. Thus, in the embodiment of FIGS. 7-10, there is no insert 255 as described above with respect to FIGS. 2-6. Those of ordinary skill in the art would recognize that this feature of either embodiment can be used interchangeably, and that proximal portion 227, 727 of either embodiment may be integral with the remainder of distal dip assembly 228, 728. Threads 725, 729 are continuous helical ridges that wrap around an outer surface of spindle 724 and an inner surface of distal tip assembly 728, respectively, to form a matched or mating pairs of threads.

In order to move distal tip spindle 724 to release suture loops 750 and thus deploy end 734 of stent-graft 730, shaft 712 is rotated. Shaft 712 is coupled to distal tip assembly 728 such that rotation of shaft 712 causes rotation of distal tip assembly 728 (i.e., they are not rotatable relative to each other). Spindle 724 is prevented from rotation due to suture loops 750. Because spindle 724 is prevented from rotating, rotation of elongate shaft 712 results relative rotation of spindle 724 and distal tip assembly 728 along threads 725, 729, thereby causing the rotational movement to be converted to translational or linear movement between spindle 724 and tip assembly 728. Because the longitudinal location of shaft 712 and distal tip assembly 728 is fixed at the proximal end (not shown in FIGS. 7-10) of inner shaft 212 via a hub or locking component (not shown), spindle 724 is longitudinally driven back or forth along the main or longitudinal axis $L_A$ of delivery system 700. If elongate shaft 712 is rotated in a first direction, i.e. clockwise or counter-clockwise depending upon the direction of the threaded connection between spindle 724 and distal tip assembly 728, spindle 724 may be distally advanced into distal tip assembly 728 to disengage retainer elements 726 of spindle 724 from suture loops 750 for final deployment of stent-graft prosthesis 730.

After first end stent 740A is permitted to deploy and suture loops 750 no longer couple first end stent 740A to retainer elements 726 of spindle 724, continued rotation of elongate shaft 712 does not result in longitudinal movement of spindle 724 because spindle 724 is no longer prevented from rotation. Rather, continued rotation of elongate shaft 712 after first end stent 740A is deployed results in spinning/rotation of spindle 724.

A delivery system with a tip capture mechanism as described above may also be utilized to deliver and deploy a stent-graft prosthesis having one or more barbs on its proximal end. Barbs are spikes or projections that radially extend from a stent when deployed in order to anchor or secure a stent-graft in place within the vasculature. In some cases a barbed stent-graft may be required or chosen due to application, i.e., an abdominal aortic aneurysm rather than a thoracic aortic aneurysm, and/or user preferences. For example, FIGS. 11, 11A, 11B, and 12 illustrate another embodiment hereof in which a delivery system 1100 having an elongated shaft 1112 has a tip capture mechanism to allow for partial deployment and repositioning of a self-expanding stent-graft prosthesis 1130 which includes at least one barb 1143 on its proximal end, although it will be understood by those of ordinary skill in the art that delivery system 1100 may be utilized to deploy stent-graft prostheses without barbs. In this embodiment, as opposed to a tip capture spindle being in threaded relationship with the distal tip assembly such that the spindle is longitudinally moved by rotation of elongate shaft 1112, a relatively short sleeve 1160 that radially constrains the end stent of the stent-graft prosthesis is in a threaded relationship with the distal tip assembly. Elongate shaft 1112 is rotated to distally advance sleeve 1160, thereby exposing or uncovering the end stent to permit self-expansion thereof.

Figure 12:
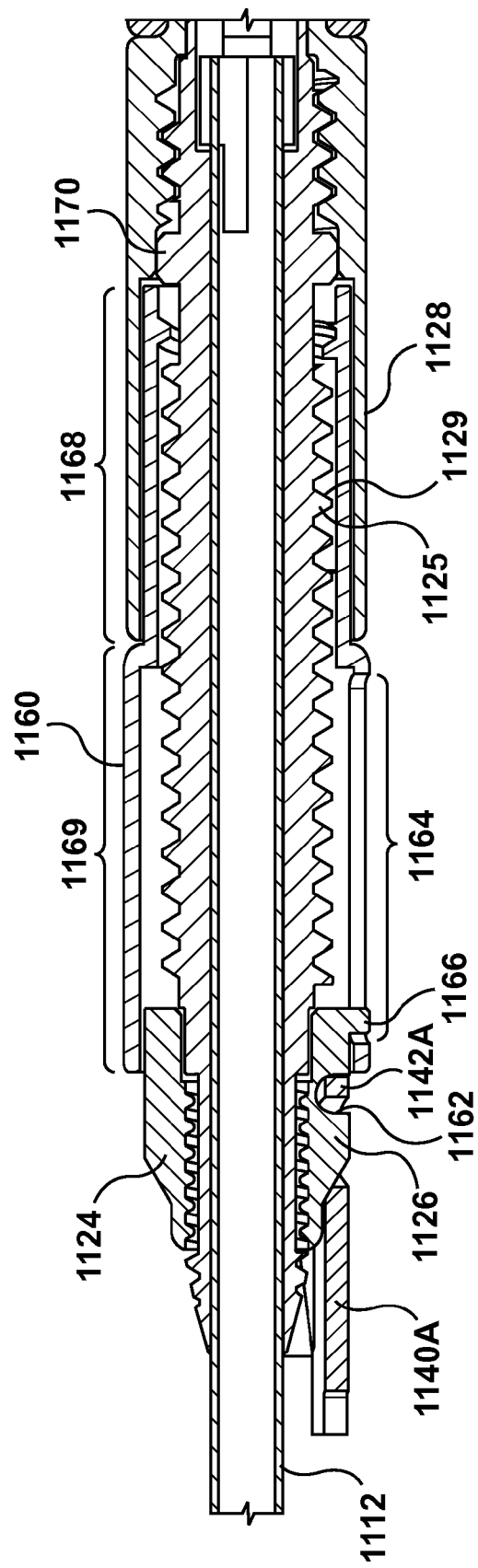
FIG. 12 is a cross-sectional view of the distal portion of the stent-graft delivery system of FIG. 11B, wherein the stent-graft prosthesis is in a fully deployed configuration.

More particularly, FIGS. 11, 11A, and 11B illustrate a distal portion of delivery system 1100 with stent-graft prosthesis 1130 in either a delivery configuration or a partially deployed configuration, and FIG. 12 illustrates a distal portion of delivery system 1100 in a deployed configuration. FIG. 11A is a cross-sectional view of FIG. 11, while FIG. 11B is an enlarged sectional view of a portion of FIG. 11A. In FIG. 12, stent-graft prosthesis 1130 is shown with first end stent 1140A undeployed for convenience of seeing the relationship between first end stent 1140A the and the delivery system 1100, but it would be understood by those having ordinary skill in the art that once sleeve 1160 is moved distally to uncover recesses 1162 and crowns 1142A, first end stent 1140A first end stent 1140A will self-expand to fully deploy stent graft prosthesis 1130, as described in more detail below. Similar to the embodiments described above, delivery system 1100 has a reduced delivery or crossing profile compared to prior delivery systems and less force to move the tip capture mechanism for final deployment of stent-graft 1130.

Elongate shaft 1112 of delivery system 1100 has a proximal end (not shown in FIGS. 11-12) and a distal end 1116. Although not shown in FIGS. 11-12, stent-graft delivery system 1100 also includes a retractable outer sheath or graft cover (not shown) to contain stent-graft prosthesis 1130 in a constrained diameter configuration while the graft delivery system is tracked through a body lumen to the deployment site. Stent-graft prosthesis 1130 is disposed around elongate shaft 1112, proximate to distal end 1116. Stent-graft prosthesis 1130 is similar to stent-graft prosthesis 230 which has an open-web or free-flow proximal end configuration, except that one or more of endmost crowns 1142A of a first end stent 1140A includes a barb 1143, although delivery system 1100 may be utilized to delivery stent-graft prostheses not having a barb thereon. Endmost crowns 1142A extend past or beyond the graft material of stent-graft prosthesis 1130 such that the endmost crowns are exposed or bare, and thus free to interact with a tip capture spindle 1124 and couple stent-graft prosthesis 1130 to delivery system 1100. For illustrative purposes, only a proximal, endmost crown 1142A having a barb 1143 of stent-graft prosthesis 1130 is shown in FIGS. 11-12.

Tip capture spindle 1124 is also disposed over elongate shaft 1112 such that tip capture spindle 1124 is rotatable relative to shaft 1112. In the delivery configuration or partially deployed configuration shown in FIGS. 11, 11A, and 11B endmost crowns 1142A engage or hook around retainer elements 1126 of tip capture spindle 1124. The number of retainer elements 1126 of tip capture spindle 1124 is equal to the number of endmost crowns 1142A of the first end stent 1140A and a single endmost crown engages or hooks around each single retainer element 1126 in a one crown to one retainer ratio. Endmost crowns 1142A are housed in a recess 1162 formed on the outer surface of a retainer 1126 of spindle 1124. Barb 1143 is radially constrained by an additional component, a relatively short sleeve 1160 which extends from first end stent 1140A to distal tip assembly 1128.

In this embodiment, distal tip assembly 1128 includes a recess or bore 1151 and a proximally-extending tubular portion 1170 is disposed within bore 1151 and extends over the outer surface of elongate shaft 1112. The bore 1151 includes female or internal threads 1153. Proximally-extending tubular portion 1170 includes external or male threads 1157 to interlock with threads 1153. Proximally-extending tubular portion 1170 in this embodiment is locked within bore 1151 and is considered part of distal tip assembly 1128. As would be understood by those of ordinary skill in the art, proximally-extending tubular portion 1170 may be connected to the remainder of distal tip assembly 1128 by other means, such as adhesives or other mechanical connectors, or may be unitary with the remainder of distal tip assembly 1128. Proximally-extending tubular portion 1170 is also coupled to distal end 1116 of elongate shaft 1112 and extends proximally therefrom. Proximally-extending tubular portion 1170 is coupled to distal end 1116 of elongate shaft 1112 such that shaft 1112 and proximally-extending tubular portion 1170 are not rotatable relative to each other.

In this embodiment, sleeve 1160 is in a threaded relationship with proximally-extending tubular portion 1170 of distal tip assembly 1128. More particularly, a proximal portion 1123 of proximally-extending tubular portion 1170 includes male or external threads 1125 formed on the outer surface thereof. At least a distal portion 1168 of sleeve 1160 includes female or internal threads 1129 on an inside surface thereof. Threads 1125, 1129 are continuous helical ridges that wrap around an outer surface of proximally-extending tubular portion 1170 and an inner surface of sleeve 1160, respectively, to form a matched or mating pairs of threads. When elongate shaft 1124 having distal tip assembly 1128 non-rotatably coupled thereto is rotated, spindle 1124 is prevented from rotation due to endmost crowns 1142A of first end stent 1140, which extend between adjacent retainer elements 1126 of spindle 1124. In addition, spindle 1124 includes a projection or extension pin 1166, which extends from spindle 1124 in a radial direction through a slot 1164 formed in sleeve 1160. With pin 1166 extending through slot 1164 of sleeve 1160, sleeve 1160 is also prevented from rotating when elongate shaft 1162 is rotated. Because sleeve 1160 is prevented from rotating and the longitudinal location of shaft 1112 and distal tip assembly 1128 is fixed at the proximal end (not shown in FIGS. 11-12) of inner shaft 1112 via a hub or locking component (not shown), rotation of elongate shaft 1112 results in sleeve 1160 being longitudinally driven back or forth along the main or longitudinal axis $L_A$ of delivery system 1100. If elongate shaft 1112 is rotated in a first direction, i.e. clockwise or counter-clockwise depending upon the direction of the threaded connection between sleeve 1160 and elongate shaft 1112, sleeve 1160 is distally advanced to uncover first end stent 1140A for final deployment of stent-graft prosthesis 1130. As sleeve 1160 moves, pin 1166 longitudinally slides within slot 1164 of sleeve 1160. Accordingly, slot 1164 is of sufficient length to allow sleeve 1160 to move distally to uncover crowns 1142A disposed in recesses 1162 on retainers 1126 of spindle 1124. Thus, in this embodiment, elongate shaft 1112 and distal assembly 1128 coupled thereto are rotated to distally advance sleeve 1160, thereby exposing or uncovering barbs 1143 and endmost crowns 1142A of first end stent 1140A which were housed within recess 1162 on retainer 1126 as shown in FIG. 12 such that first end stent 1140A of stent-graft prosthesis 1130 is permitted to fully expand or deploy.

In an embodiment, sleeve 1160 may have a stepped outer diameter in which a distal portion 1168 of the sleeve has a smaller outer diameter than a proximal portion 1169 of the sleeve. In the delivery or partially deployed configurations, proximal portion 1169 covers and restrains first end stent 1140A of stent-graft prosthesis 1130. When elongate shaft 1112 is rotated to distally advance sleeve 1160, distal portion 1168 of sleeve 1160 slides into a proximal portion of distal tip assembly 1128 and proximal portion 1169 of sleeve 1160 moves in a distal direction to uncover first end stent 1140A. Rotation of elongate shaft 1112 continues to distally advance sleeve 1160 until pin 1166 abuts against the proximal end or edge of slot 1164, at which point proximal portion 1169 of sleeve 1160 no longer covers or constrains endmost crowns 1142A and end stent 1140A is permitted to deploy.

After first end stent 1140A is permitted to deploy and endmost crowns 1142A of first end stent 1140A no longer extend between adjacent retainer elements 1126 of spindle 1124, continued rotation of elongate shaft 1112 does not result in longitudinal movement of spindle 1124 because spindle 1124 is no longer prevented from rotation. Rather, continued rotation of elongate shaft 1112 after first end stent 1140A is deployed results in spinning/rotation of spindle 1124.

Although the embodiment of FIGS. 11-12 are described with proximally-extending tubular portion 1170 being considered part of distal tip assembly 1128, it will be apparent to one of ordinary skill in the art that proximally-extending tubular portion 1170 having threads 1125 thereof may be mounted over a distal portion of elongate shaft 1112. Since elongate shaft 1112 and distal tip assembly 1128 are coupled together to rotate simultaneously, the operation of the embodiment of FIGS. 11-12 is unaltered if proximally-extending tubular portion 1170 is mounted over and attached to elongate shaft 1112 such proximally-extending tubular portion 1170 rotates with elongate shaft 1112.

FIGS. 13, 13A, 13B, 14A, and 14B illustrate another embodiment hereof in which a delivery system 1300 has a tip capture mechanism to allow for partial deployment and repositioning of a self-expanding stent-graft prosthesis 1330 which includes at least one barb 1343 on its proximal end, although it will be understood by those of ordinary skill in the art that delivery system 1300 may be utilized to deploy stent-graft prostheses not having any barbs. FIGS. 13, 13A, and 13B illustrate a distal portion of delivery system 1300 with stent-graft prosthesis 1330 in either a delivery configuration or a partially deployed configuration, and FIGS. 14A and 14B illustrate a distal portion of delivery system 1300 in a deployed configuration. In FIGS. 14A and 14B, stent-graft prosthesis 1330 is still shown with first end stent 1340A undeployed for convenience of seeing the relationship between first end stent 1340A the and the delivery system 1300, but it would be understood by those having ordinary skill in the art that once sleeve 1160 does not cover recesses 1362 and crowns 1342A, first end stent 1340A will self-expand to fully deploy stent graft prosthesis 1330, as described in more detail below. FIG. 13A is a cross-sectional view of FIG. 13, while FIG. 13B is an enlarged sectional view of a portion of FIG. 13A and FIG. 14B is an enlarged sectional view of a portion of FIG. 14A. Similar to the embodiments described above, delivery system 1300 has a reduced delivery or crossing profile compared to prior delivery systems and requires less force to move the tip capture mechanism for final deployment of stent-graft 1330. In this embodiment, a relatively short sleeve 1360 distally advances to uncover and fully deploy stent-graft prosthesis 1330 as described above with respect to sleeve 1160. However, unlike the embodiment of FIGS. 11-12, a tip capture spindle 1324 of delivery system 1300 also concurrently moves in a proximal longitudinal direction during final deployment of stent-graft prosthesis 1330. By having two components that concurrently move in opposing directions, stent-graft prosthesis 1330 is fully deployed by half the rotations of embodiments having only one moving component as will be explained in more detail herein.

More particularly, delivery system 1300 includes an elongate shaft 1312 having a proximal end (not shown in FIGS. 13-14) and a distal end 1316, and a tapered distal tip assembly 1328 is coupled to distal end 1316 of elongate shaft 1312 such that distal end assembly 1328 is not rotatable or slideable relative to shaft 1312. Although not shown in FIGS. 13-14, stent-graft delivery system 1300 also includes a retractable outer sheath or graft cover (not shown) to contain stent-graft prosthesis 1330 in a constrained diameter configuration while the graft delivery system is tracked through a body lumen to the deployment site. Stent-graft prosthesis 1330 is disposed around elongate shaft 1312, proximate to distal end 1316. Stent-graft prosthesis 1330 is similar to stent-graft prosthesis 1130 which has an open-web or free-flow proximal end configuration and one or more endmost crowns 1342A of a first end stent 1340A include a barb 1343, although delivery system 1300 may be utilized to delivery stent-graft prostheses not having a barb thereon. Endmost crowns 1342A extend past or beyond the graft material of stent-graft prosthesis 1330 such that the endmost crowns are exposed or bare, and thus free to interact with tip capture spindle 1324 and couple stent-graft prosthesis 1330 to delivery system 1300. For illustrative purposes, only a proximal, endmost crown 1342A having a barb 1343 of stent-graft prosthesis 1330 is shown in FIGS. 13-14. Delivery system 1300 may include a fitting 1378 adjacent to first end stent 1340A. Fitting 1378 is formed from an elastomer material such as rubber, and essentially functions as a shock absorber that minimizes the space between end stent 1340A and elongate shaft 1312. If stent-graft prosthesis 1330 is repositioned after initial deployment, fitting 1378 absorbs and dissipates energy resulting from the movement of elongate shaft 1312 during repositioning to prevent unintentional movement of first end stent 1340A.

Tip capture spindle 1324 is disposed around elongate shaft 1312 such that spindle 1324 is rotatable and slideable relative to shaft 1312. In the delivery configuration or partially deployed configuration shown in FIGS. 13, 13A, and 13B endmost crowns 1342A engage or hook around retainer elements 1326 of tip capture spindle 1324. The number of retainer elements 1326 of tip capture spindle 1324 is equal to the number of endmost crowns 1342A of the first end stent and a single endmost crown engages or hooks around each retainer element 1326 in a one crown to one retainer ratio. Endmost crowns 1342A are housed in a recess 1362 formed on the outer surface of a retainer 1326 of spindle 1324. Barb 1343 is radially constrained by relatively short sleeve 1360 which extends from first end stent 1340A to distal tip assembly 1328.

In this embodiment, distal tip assembly 1328 includes a recess or bore 1351 and a proximally-extending tubular portion 1370 is disposed within bore 1351. The bore 1351 includes female or internal threads 1353. Proximally-extending tubular portion 1370 includes external or male threads 1357 to interlock with threads 1353. Proximally-extending tubular portion 1370 in this embodiment is locked within bore 1351 and is considered part of distal tip assembly 1328. As would be understood by those of ordinary skill in the art, proximally-extending tubular portion 1370 may be connected to the remainder of distal tip assembly 1328 by other means, such as adhesives or other mechanical connectors, or may be unitary with the remainder of distal tip assembly 1328. Proximally-extending tubular portion 1370 is also coupled to distal end 1316 of elongate shaft 1312 and extends proximally therefrom. Proximally-extending tubular portion 1370 is coupled to distal end 1316 of elongate shaft 1312 such that shaft 1312 and proximally-extending tubular portion 1370 are not rotatable relative to each other. A spherical ball 1372 is held or housed within a hole or opening 1374 formed within proximally-extending portion 1370 of distal tip assembly 1328. Sleeve 1360 extends over an outer surface of proximally-extending portion 1370, and includes a continuous helical or spiral groove 1329 on an inside surface thereof. Groove 1329 is semi-circular or concave and sized to receive or house half of ball 1372. At least a distal portion 1323 of spindle 1324 extends within a bore or lumen 1358 of proximally-extending portion 1370 and includes a continuous helical or spiral groove 1325 on an outer surface thereof. Groove 1325 is also semi-circular or concave and sized to receive or house half of ball 1372. Groove 1329 of sleeve 1360 aligns with groove 1325 of spindle 1324 to create a continuous helical or spiral passageway that is spherical and sized to house ball 1372. In the delivery or partially deployed configuration of FIGS. 13, 13A, and 13B, ball 1372 extends through hole 1374 of proximally-extending portion 1370 with a first or "top" half of the ball 1372 housed within groove 1329 of sleeve 1360 and a second or "bottom" half of the ball 1372 housed within groove 1325 of spindle 1324. Grooves 1325, 1329 have the same pitch but the pitch is in opposing directions, i.e., grooves 1325 have a left hand thread while grooves 1329 have a right hand thread or vice versa.

When elongate shaft 1312 and distal tip assembly 1328 coupled thereto is rotated, sleeve 1360 is distally and spindle 1324 is simultaneously proximally retracted to uncover recesses 1362 in retaining elements 1326 to fully deploy first end stent 1340A of stent-graft prosthesis 1330. More particularly, when elongate shaft 1312 is rotated, spindle 1324 is prevented from rotation due to endmost crowns 1342A of first end stent 1340, which extend between adjacent retainer elements 1326 of spindle 1324. In addition, spindle 1324 includes a projection or extension pin 1366, which extends from spindle 1324 in a radial direction through a slot 1364 formed in sleeve 1360. With pin 1366 extending through slot 1364 of sleeve 1360, sleeve 1360 is also prevented from rotating when elongate shaft 1362 is rotated. However, when elongate shaft 1312 is rotated, proximal-extending portion 1370 of distal tip assembly 1328 rotates and thereby causes ball 1372 to spin or rotate. Ball 1372 spins but remains in the same longitudinal position, extending through hole 1374 of proximally-extending portion 1370. Since the longitudinal location of shaft 1312 and distal tip assembly 1328 is fixed at the proximal end (not shown in FIGS. 13-14) of inner shaft 1312 via a hub or locking component (not shown), rotation/spinning of ball 1372 within the continuous helical passageway formed by grooves 1325, 1329 of sleeve 1360, spindle 1324, respectively, causes or drives sleeve 1360 and spindle 1324 in opposing directions along the main or longitudinal axis $L_A$ of delivery system 1300. Because the pitch of grooves 1325, 1329 of spindle 1324 and sleeve 1360, respectively, are in opposing longitudinal directions, spindle 1324 is driven in a proximal direction and sleeve 1360 is driven in a distal direction, thereby exposing or uncovering barbs 1343 and endmost crowns 1342A of first end stent 1340A which were housed within recess 1362 on retainer 1326 as shown in FIGS. 14A and 14B such that first end stent 1340A of stent-graft prosthesis 1330 is permitted to fully expand or deploy. As sleeve 1360 moves, pin 1366 longitudinally slides within slot 1364 of sleeve 1360. Accordingly, slot 1364 is of sufficient length to allow sleeve 1360 to move distally to uncover crowns 1342A disposed in recesses 1362 on retainers 1326 of spindle 1324. Pin 1366 ensures that spindle 1324 and sleeve 1360 move at the same time and at the same rate. Without pin 1366, one of the spindle or the sleeve could move through its range of motion without the other part advancing at all. However, pin 1366 balances the forces between the two moving parts. By having two components moving at the same time in opposing or opposite directions, i.e., sleeve 1360 and spindle 1324, deployment of stent-graft prosthesis 1330 is achieved via half the rotations of embodiments having only one moving component. Two moving components have a finer pitch and provide a mechanical advantage compared to embodiments having only one moving component.

After first end stent 1340A is permitted to deploy and endmost crowns 1342A of first end stent 1340A no longer extend between adjacent retainer elements 1326 of spindle 1324, continued rotation of elongate shaft 1312 does not result in longitudinal movement of spindle 1324 and sleeve 1360 because spindle 1324 and sleeve 1360 are no longer prevented from rotation. Rather, continued rotation of elongate shaft 1312 after first end stent 1340A is deployed results in spinning/rotation of spindle 1324 and sleeve 1360.

In an embodiment, sleeve 1360 may have a stepped outer diameter similar to sleeve 1160 in which a distal portion 1368 of the sleeve has a smaller outer diameter than a proximal portion 1369 of the sleeve. When elongate shaft 1312 is rotated to distally advance sleeve 1360, distal portion 1368 of sleeve 1360 retreats or slides into a proximal portion of distal tip assembly 1328 and proximal portion 1369 of sleeve 1360 moves in a distal direction to uncover first end stent 1340A. Rotation of elongate shaft 1312 continues to distally advance sleeve 1360 until pin 1366 abuts against the proximal end or edge of slot 1364, at which point proximal portion 1369 of sleeve 1360 no longer covers or constrains endmost crowns 1342A and end stent 1340A is permitted to deploy.

In addition, as shown in FIGS. 13-14, delivery system 1300 may include a relatively short hypotube 1376 which extends over an outer surface of a distal portion of elongate shaft 1312 from first end stent 1340A, or a proximal end of spindle 1324, to distal end 1316 of elongate shaft 1312. Hypotube 1376 may be formed from stainless steel or other relatively stiff material, and provides pushability and stability to the distal portion of elongate shaft 1312 which may be formed from Nitinol (NiTi). Elongate shaft 1312 rotates within hyptotube 1376, and distal tip assembly 1328 including proximally-extending portion 1370 rotates around hypotube 1376. Hypotube 1376 may be included in any delivery system embodiment described herein.

FIGS. 15, 16, and 16A illustrate yet another embodiment hereof in which a delivery system 1500 has a tip capture mechanism to allow for partial deployment and repositioning of a self-expanding stent-graft prosthesis 1530 which includes at least one barb 1543 on its proximal end, although it will be understood by those of ordinary skill in the art that delivery system 1500 may be utilized to deploy stent-graft prostheses not having any barbs. FIG. 15 illustrates a distal portion of delivery system 1500 with stent-graft prosthesis 1530 in either a delivery configuration or a partially deployed configuration, and FIG. 16 illustrates a distal portion of delivery system 1500 in a deployed configuration. In FIG. 14, stent-graft prosthesis 1530 is still shown with first end stent 1540A undeployed for convenience of seeing the relationship between first end stent 1540A the and the delivery system 1500, but it would be understood by those having ordinary skill in the art that once sleeve 1560 does not cover recesses 1562 and crowns 1542A, first end stent 1540A will self-expand to fully deploy stent graft prosthesis 1530, as described in more detail below. FIG. 16A is a cross-sectional perspective view of FIG. 16, with stent-graft prosthesis 1530 and elongate shaft 1512 removed for illustrative purposes. Similar to the embodiments described above, delivery system 1500 has a reduced delivery or crossing profile compared to prior delivery systems and less force is required to move the tip capture mechanism for final deployment of stent-graft 1530. Similar to the embodiment of FIGS. 13-14, a sleeve 1560 distally advances to uncover and fully deploy stent-graft prosthesis 1530 and a tip capture spindle 1524 of delivery system 1500 proximally retracts during final deployment of stent-graft prosthesis 1530. By having two components that concurrently move in opposing directions, stent-graft prosthesis 1530 is fully deployed by half the rotations of embodiments having only one moving component. However, this embodiment utilizes a double threaded configuration to simultaneously move sleeve 1560 and spindle 1524 rather than a spinning ball.

More particularly, delivery system 1500 includes an elongate shaft 1512 having a proximal end (not shown in FIGS. 15-16) and a distal end (not shown in the view of FIGS. 15-16), and a tapered distal tip assembly 1528 is coupled to the distal end of elongate shaft 1512. Although not shown in FIGS. 15-16, stent-graft delivery system 1500 also includes a retractable outer sheath or graft cover (not shown) to contain stent-graft prosthesis 1530 in a constrained diameter configuration while the graft delivery system is tracked through a body lumen to the deployment site. Stent-graft prosthesis 1530 is disposed around elongate shaft 1512, proximate to the distal end. Stent-graft prosthesis 1530 is similar to stent-graft prosthesis 1130 which has an open-web or free-flow proximal end configuration and one or more endmost crowns 1542A of a first end stent 1540A includes a barb 1543, although delivery system 1500 may be utilized to delivery stent-graft prostheses not having a barb thereon. Endmost crowns 1542A extend past or beyond the graft material of stent-graft prosthesis 1530 such that the endmost crowns are exposed or bare, and thus free to interact with tip capture spindle 1524 and couple stent-graft prosthesis 1530 to delivery system 1500. For illustrative purposes, only a proximal, endmost crown 1542A having a barb 1543 of stent-graft prosthesis 1530 is shown in FIGS. 15-16.

Tip capture spindle 1524 is also disposed over elongate shaft 1512 such that tip capture spindle 1524 is rotatable and slideable relative to shaft 1512. In the delivery configuration or partially deployed configuration shown in FIG. 15, endmost crowns 1542A engage or hook around retainer elements 1526 of tip capture spindle 1524. The number of retainer elements 1526 of tip capture spindle 1524 is equal to the number of endmost crowns 1542A of the first end stent 1540A and a single endmost crown engages or hooks around each single retainer element 1526 in a one crown to one retainer ratio. Endmost crowns 1542A are housed in a recess 1562 formed on the outer surface of a retainer 1526 of spindle 1524. Barb 1543 is radially constrained by relatively short sleeve 1560 which extends from first end stent 1540A to distal tip assembly 1528.

In this embodiment, distal tip assembly 1528 includes a recess or bore 1551 and a proximally-extending tubular portion 1570 is disposed within bore 1551. The bore 1551 includes female or internal threads 1553. Proximally-extending tubular portion 1570 includes external or male threads 1557 to interlock with threads 1553. Proximally-extending tubular portion 1570 in this embodiment is locked within bore 1551 and is considered part of distal tip assembly 1528. As would be understood by those of ordinary skill in the art, proximally-extending tubular portion 1570 may be connected to the remainder of distal tip assembly 1528 by other means, such as adhesives or other mechanical connectors, or may be unitary with the remainder of distal tip assembly 1528. Proximally-extending tubular portion 1570 is also coupled to the distal end of elongate shaft 1512 and extends proximally therefrom. Proximally-extending tubular portion 1570 is coupled to the distal end of elongate shaft 1512 such that shaft 1512 and proximally-extending tubular portion 1570 are not rotatable relative to each other. An inner surface of proximally-extending portion 1570 is in a threaded relationship with spindle 1524, and an outer surface of proximally-extending portion 1570 is in a threaded relationship with sleeve 1560. As to the first threaded relationship between spindle 1524 and proximally-extending portion 1570 of distal tip assembly 1528, at least a distal portion 1523 of spindle 1524 extends within a bore or lumen 1558 of proximally-extending portion 1570 and includes male or external threads 1525 formed on the outer surface of the spindle. At least a distal portion 1527 of proximally-extending portion 1570 includes female or internal threads 1529 on an inside surface thereof. Threads 1525, 1529 are continuous helical ridges that wrap around an outer surface of spindle 1524 and an inner surface of proximally-extending portion 1570, respectively, to form a matched or mating pairs of threads. As to the second threaded relationship between proximally-extending portion 1570 of distal tip assembly 1528 and sleeve 1560, a portion 1580 of proximally-extending portion 1570 includes male or external threads 1582 formed on the outer surface of proximally-extending portion 1570. Sleeve 1560 extends over an outer surface of proximally-extending portion 1570 and at least a distal portion 1584 of sleeve 1560 includes female or internal threads 1586 on an inside surface thereof. Threads 1582, 1586 are continuous helical ridges that wrap around an outer surface of proximally-extending portion 1570 and an inner surface of sleeve 1560, respectively, to form a matched or mating pairs of threads. Mating pair of threads 1525, 1529 have the same pitch as mating pair of threads 1582, 1586, but the pitch is in opposing directions, i.e., threads 1525, 1529 have a left hand thread while threads 1582, 1586 have a right hand thread or vice versa.

When elongate shaft 1512 and distal tip assembly 1528 coupled thereto are rotated, sleeve 1560 is distally advanced into distal tip assembly 1528 and spindle 1524 is simultaneously proximally retracted to fully deploy first end stent 1540A of stent-graft prosthesis 1530. More particularly, when elongate shaft 1512 is rotated, spindle 1524 is prevented from rotation due to endmost crowns 1542A of first end stent 1540, which extend between adjacent retainer elements 1526 of spindle 1524. In addition, spindle 1524 includes a projection or extension pin 1566, which extends from spindle 1524 in a radial direction through a slot 1564 formed in sleeve 1560. With pin 1566 extending through slot 1564 of sleeve 1560, sleeve 1560 is also prevented from rotating when elongate shaft 1562 is rotated. Because sleeve 1560 and spindle 1524 are prevented from rotating and the longitudinal location of shaft 1512 and distal tip assembly 1528 is fixed at the proximal end (not shown in FIGS. 15-16) of inner shaft 1512 via a hub or locking component (not shown), rotation of elongate shaft 1512 results in both sleeve 1560 and spindle 1524 being longitudinally driven back or forth along the main or longitudinal axis $L_4$ of delivery system 1500. Because threads 1525, 1529 have a left hand thread while threads 1582, 1586 have a right hand thread, spindle 1524 is driven in a proximal direction and sleeve 1560 is driven in a distal direction thereby exposing or uncovering barbs 1543 and endmost crowns 1542A of first end stent 1540A which were housed within recess 1562 on retainer 1526 as shown in FIG. 16 such that first end stent 1540A of stent-graft prosthesis 1530 is permitted to fully expand or deploy. As sleeve 1560 moves, pin 1566 longitudinally slides within slot 1564 of sleeve 1560. Accordingly, slot 1564 is of sufficient length to allow sleeve 1560 to move distally to uncover crowns 1542A disposed in recesses 1562 on retainers 1526 of spindle 1524. Pin 1566 ensures that spindle 1524 and sleeve 1560 move at the same time and at the same rate, as described above with respect to pin 1366.

In an embodiment, sleeve 1560 may have a stepped outer diameter similar to sleeve 1160 in which a distal portion 1568 of the sleeve has a smaller outer diameter than a proximal portion 1569 of the sleeve. When elongate shaft 1512 is rotated to distally advance sleeve 1560, distal portion 1568 of sleeve 1560 retreats or slides into a proximal portion of distal tip assembly 1528 and proximal portion 1569 of sleeve 1560 moves in a distal direction to uncover first end stent 1540A. Rotation of elongate shaft 1512 continues to distally advance sleeve 1560 until pin 1566 abuts against the proximal end or edge of slot 1564, at which point proximal portion 1569 of sleeve 1560 no longer covers or constrains endmost crowns 1542A and end stent 1540A is permitted to deploy.

After first end stent 1540A is permitted to deploy and endmost crowns 1542A of first end stent 1540A no longer extend between adjacent retainer elements 1526 of spindle 1524, continued rotation of elongate shaft 1512 does not result in longitudinal movement of spindle 1524 and sleeve 1560 because spindle 1524 and sleeve 1560 are no longer prevented from rotation. Rather, continued rotation of elongate shaft 1512 after first end stent 1540A is deployed results in spinning/rotation of spindle 1524 and sleeve 1560.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. For example, in the above embodiments, the scaffolding or support of the stent-graft prostheses have been illustrated as a series of independent or separate self-expanding stents/sinusoidal patterned rings. However, as will be understood by those of ordinary skill in the art, the support structure or scaffolding of a stent-graft prosthesis may have other configurations such as a series of sinusoidal patterned rings coupled to each other to form a self-expanding stent. In another embodiment, the support structure or scaffolding of a stent-graft prosthesis may be a unitary tubular component having diamond-shaped opening, which may be formed by various conventional stent forming methods as would be understood by one of ordinary skill in the art. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A stent-graft delivery system comprising:
 an elongate shaft;
 a tip capture spindle disposed over the shaft, proximate to a distal end of the shaft, wherein a proximal portion of the tip capture spindle includes a plurality of retainer elements configured to engage a stent of a stent-graft prosthesis and a distal portion of the tip capture spindle includes a continuous helical groove on an outer surface thereof;
 a distal tip assembly coupled to the distal end of the shaft, wherein a proximally-extending portion of the distal tip assembly proximally extends over the outer surface of the distal portion of the tip capture spindle;
 a sleeve having a proximal end extending over the retainer elements of the tip capture spindle and a distal end extending over the proximally-extending portion of the distal tip assembly, wherein an inner surface of the sleeve includes a continuous helical groove that aligns with the continuous helical groove on the outer surface of the tip capture spindle to create a continuous helical passageway;
 a spherical ball extending through an opening formed within the proximally-extending portion of the distal tip assembly, wherein a first half of the ball is housed within the helical groove of the sleeve and a second half of the ball is housed within the helical groove of the tip capture spindle;
 wherein rotation of the elongate shaft rotates the distal tip assembly, thereby spinning the ball within the continuous helical passageway and resulting in longitudinal movement of the tip capture spindle and the sleeve.

2. The stent-graft delivery system of claim 1, further comprising:
   a retractable outer sheath defining a lumen, wherein the elongate shaft is slidingly received within the lumen of the outer sheath.

3. The stent-graft delivery system of claim 1, further comprising:
   a stent graft prosthesis mounted over the shaft, proximate to the tip capture spindle, wherein the stent graft prosthesis includes a radially-compressible stent coupled to a tubular graft.

4. The stent-graft delivery system of claim 3, wherein endmost crowns of the stent engage the plurality of retainer elements of the tip capture spindle.

5. The stent-graft delivery system of claim 4, wherein at least one endmost crown includes a radially extending barb that anchors the stent-graft in place within the vasculature after deployment.

6. The stent-graft delivery system of claim 3, wherein the sleeve has a stepped outer diameter in which a distal portion of the sleeve has a smaller outer diameter than a proximal portion of the sleeve, and the proximal portion of the sleeve covers and restrains the endmost crowns of the stent when the stent-graft prosthesis is in a delivery configuration or a partially-deployed configuration.

7. The stent-graft delivery system of claim 1, wherein a pitch of the continuous helical groove of the sleeve and a pitch of the continuous helical groove of the tip capture spindle are in opposing longitudinal directions.

8. The stent-graft delivery system of claim 7, wherein rotation of the elongate shaft moves the tip capture spindle in a proximal direction and the sleeve in a distal direction.

9. The stent-graft delivery system of claim 1, wherein the tip capture spindle includes a radially-extending pin that extends through a slot formed in the sleeve.

10. The stent-graft delivery system of claim 1, further comprising:
    a hypotube which extends over an outer surface of a distal portion of the elongate shaft from at least a proximal end of the tip capture spindle to the distal end of the elongate shaft.

11. The stent-graft delivery system of claim 10, wherein the hypotube is formed from stainless steel and the elongate shaft is formed from Nitinol.

12. A method of deploying a stent-graft prosthesis, wherein the method comprises the steps of:
    percutaneously advancing a delivery system having a stent-graft prosthesis mounted on an elongate shaft, wherein a tip capture spindle is disposed over the shaft, a proximal portion of the tip capture spindle including a plurality of retainer elements engaged with a stent of the stent-graft prosthesis and a distal portion of the tip capture spindle including a continuous helical groove on an outer surface thereof, wherein a distal tip assembly is coupled to a distal end of the shaft, a proximally-extending portion of the distal tip assembly proximally extends over the outer surface of the distal portion of the tip capture spindle, and wherein a sleeve having a proximal end extends over the retainer elements of the tip capture spindle and a distal end extends over the proximally-extending portion of the distal tip assembly, an inner surface of the sleeve including a continuous helical groove that aligns with the continuous helical groove on the outer surface of the tip capture spindle to create a continuous helical passageway, and wherein a spherical ball extends through an opening formed within the proximally-extending portion of the distal tip assembly and a first half of the ball is housed within the continuous helical groove of the sleeve and a second half of the ball is housed within the continuous helical groove of the tip capture spindle;
    positioning the stent-graft prosthesis;
    partially deploying the stent-graft prosthesis by retracting an outer sheath of the delivery system to expose the stent-graft prosthesis, wherein the stent-graft prosthesis self-expands and the stent remains engaged with the plurality of retainer elements of the tip capture spindle;
    rotating the elongate shaft to fully deploy the stent-graft prosthesis, wherein rotation of the elongate shaft rotates the distal tip assembly, thereby spinning the ball within the continuous helical passageway and resulting in longitudinal movement of the tip capture spindle and the sleeve.

13. The method of claim 12, further comprising the step of:
    repositioning the partially deployed stent-graft prosthesis, wherein the repositioning step is performed prior to the step of rotating the elongate shaft to fully deploy the stent-graft prosthesis.

14. The method of claim 12, wherein the sleeve has a stepped outer diameter in which a distal portion of the sleeve has a smaller outer diameter than a proximal portion of the sleeve, and the proximal portion of the sleeve covers and restrains endmost crowns of the stent when the stent-graft prosthesis is in a delivery configuration or a partially-deployed configuration.

15. The method of claim 12, wherein a pitch of the continuous helical groove of the sleeve and a pitch of the continuous helical groove of the tip capture spindle are in opposing longitudinal directions.

16. The method of claim 12, wherein rotation of the elongate shaft moves the tip capture spindle in a proximal direction and the sleeve in a distal direction.

17. The method of claim 12, wherein the tip capture spindle includes a radially-extending pin that extends through a slot formed in the sleeve.

18. The method of claim 12, wherein the delivery system further includes a hypotube which extends over an outer surface of a distal portion of the elongate shaft from at least a proximal end of the tip capture spindle to the distal end of the elongate shaft.

19. The method of claim 18, wherein the hypotube is formed from stainless steel and the elongate shaft is formed from Nitinol.

20. The method of claim 12, wherein endmost crowns of the stent engage the plurality of retainer elements of the tip capture spindle.

* * * * *